United States Patent
Wu et al.

(10) Patent No.: US 11,725,053 B2
(45) Date of Patent: Aug. 15, 2023

(54) CHIMERIC ANTIGEN RECEPTORS COMPRISING A HUMAN TRANSFERRIN EPITOPE SEQUENCE

(71) Applicants: ProMab Biotechnologies, Inc., Richmond, CA (US); Forevertek Biotechnology Co., Ltd, Changsha (CN)

(72) Inventors: Lijun Wu, Albany, CA (US); Vita Golubovskaya, Richmond, CA (US)

(73) Assignees: ProMab Biotechnologies, Inc., Richmond, CA (US); Forevertek Biotechnology Co., Ltd, Changsha (CN)

(*) Notice: Subject to any disclaimer, the term of this patent is extended or adjusted under 35 U.S.C. 154(b) by 101 days.

(21) Appl. No.: 16/905,609

(22) Filed: Jun. 18, 2020

(65) Prior Publication Data

US 2020/0354451 A1 Nov. 12, 2020

Related U.S. Application Data

(63) Continuation of application No. PCT/US2018/067083, filed on Dec. 21, 2018.
(Continued)

(51) Int. Cl.
*C07K 16/46* (2006.01)
*C07K 16/28* (2006.01)
(Continued)

(52) U.S. Cl.
CPC ...... *C07K 16/2803* (2013.01); *C07K 14/7051* (2013.01); *C07K 14/70521* (2013.01);
(Continued)

(58) Field of Classification Search
None
See application file for complete search history.

(56) References Cited

U.S. PATENT DOCUMENTS 10,835,604 B2 * 11/2020 Ngwa .............. A61P 35/04
11,034,763 B2 * 6/2021 Wu ............... A61K 35/17
(Continued)

FOREIGN PATENT DOCUMENTS

WO 2017172952 A1 10/2017

OTHER PUBLICATIONS

Xu et al.,The basics of CAR T design and challenges in immunotherapy of solid tumors—Ovarian cancer as a model, Human Vacc. Immunother. 13(7):1548-1555, Jun. 2017.*
(Continued)

*Primary Examiner* — Claire Kaufman
(74) *Attorney, Agent, or Firm* — Perkins Coie LLP; Viola Kung

(57) ABSTRACT

The present invention is directed to a chimeric antigen receptor fusion protein comprising: (i) a single-chain variable fragment (scFv) comprising $V_H$ and $V_L$, wherein scFv has an activity against a tumor antigen, (ii) a transmembrane domain, (iii) at least one co-stimulatory domains, and (iv) an activating domain; wherein the CAR further comprises a human transferrin fragment, which is an epitope for an antibody against human transferrin, at N-terminus or C-terminus to scFv, or between $V_H$ and $V_L$. Preferred tumor antigens are CD19, CD22 and BCMA. The CD19-TF-CAR-T cells, CD22-TF-CAR-T cells, and BAMA-TF CAR-T cells secrete less cytokines, but they have the same efficacy against cancer target cells when comparing with same CAR without TF.

17 Claims, 9 Drawing Sheets

Specification includes a Sequence Listing.

Related U.S. Application Data

(60) Provisional application No. 62/609,541, filed on Dec. 22, 2017.

(51) Int. Cl.
    *C07K 14/725*    (2006.01)
    *C07K 14/705*    (2006.01)
    *A61K 39/00*     (2006.01)
    *C07K 14/79*     (2006.01)

(52) U.S. Cl.
    CPC .... *C07K 16/2878* (2013.01); *A61K 2039/505* (2013.01); *C07K 14/79* (2013.01); *C07K 2317/622* (2013.01); *C07K 2317/73* (2013.01); *C07K 2319/03* (2013.01); *C07K 2319/33* (2013.01)

(56) References Cited

U.S. PATENT DOCUMENTS

| | | |
|---|---|---|
| 2007/0066813 A1 | 3/2007 | Prior et al. |
| 2010/0215651 A1 | 8/2010 | Blein et al. |
| 2011/0093962 A1 | 4/2011 | Heidbrink et al. |
| 2014/0056896 A1 | 2/2014 | Tedder et al. |
| 2014/0271635 A1 | 9/2014 | Brogdon et al. |
| 2016/0096902 A1 | 4/2016 | Cooper et al. |

OTHER PUBLICATIONS

Chen et al., Fusion protein linkers: Property, design and functionality, Adv. Drug Deliv. Rev. 65:1357-1369, 2013.*

Gong et al., Chimeric antigen receptor natural killer (CAR-NK) cell design and engineering for cance therapy, J. Hematol. Oncol. 14: 73, 35 pages, 2021.*

GenBank_AAB97880, transferrin, partial [*Homo sapiens*], Jul. 24, 2016, retrieved on Feb. 21, 2019.

Alabanza et al., "Function of Novel Anti-CD19 Chimeric Antigen Receptors with Human Variable Regions Is Affected by Hinge and Transmembrane Domains", Mol Ther. Nov. 2017, vol. 25(11), p. 2452-2465. Epub Jul. 27, 2017.

White et al., "Monoclonal antibodies against defined epitopes of the human transferrin receptor cytoplasmic tail", Biochim Biophys Acta. 1992, vol. 1136(1), p. 28-34.

International Search Report dated May 3, 2019 cited in PCT/US18/67083.

* cited by examiner

CHIMERIC ANTIGEN RECEPTORS COMPRISING A HUMAN TRANSFERRIN EPITOPE SEQUENCE

This application is a continuation of PCT/US2018/067083, filed Dec. 21, 2018; which claims the priority of U.S. Provisional Application No. 62/609,541, filed Dec. 22, 2017. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Dec. 12, 2018, and a size of 8000 bytes. The Sequence Listing filed via EFS-Web is part of the specification and is hereby incorporated in its entirety by reference herein.

FIELD OF THE INVENTION

The present invention relates to a nucleic acid encoding a chimeric antigen receptor (CAR) and a cell expressing a chimeric antigen receptor, which are useful in the field of adoptive immunity gene therapy for tumors. The invention particularly relates CAR comprising a human transferrin epitope sequence (TF) such as CD19-TF-CAR, CD22-TF-CAR and BCMA-TF-CAR.

BACKGROUND OF THE INVENTION

Immunotherapy is emerging as a highly promising approach for the treatment of cancer. T cells or T lymphocytes, the armed forces of our immune system that constantly looks for foreign antigens and discriminates abnormal (cancer or infected cells) from normal cells [1]. Genetically modifying T cells with CARs is the most common approach to design tumor-specific T cells. CAR-T cells targeting tumor-associated antigens (TAA) can be infused into patients (called adoptive cell transfer or ACT) representing an efficient immunotherapy approach [1, 2]. The advantage of CAR-T technology compared with chemotherapy or antibody is that reprogrammed engineered T cells can proliferate and persist in the patient ("a living drug")[3], [4].

CARs (Chimeric antigen receptors) usually consist of a monoclonal antibody-derived single-chain variable fragment (scFv) linked by a hinge and then transmembrane domain to a variable number of intracellular signaling domains: a single, cellular activating, CD3-zeta domain; and CD28, CD137 (4-1BB) or other co-stimulatory domains, in tandem with a CD3-zeta domain (the CD27 signaling domain has also been used in the place of either the CD28 or CD137 domain) (FIG. 1) [3], [5]. The evolution of CARs went from first generation (with no co-stimulation domains) to second generation (with one co-stimulation domain) to third generation CAR (with several co-stimulation domains). Generating CARs with multiple costimulatory domains (the so-called $3^{rd}$ generation CAR) have led to increased cytolytic activity, and significantly improved persistence of CAR-T cells that demonstrate augmented anti-tumor activity.

Transferrins are iron-binding transport proteins which can bind two $Fe^{3+}$ ions in association with the binding of an anion. It is responsible for the transport of iron from sites of absorption and heme degradation to those of storage and utilization. Serum transferrin may also have a further role in stimulating cell proliferation. Transferrins are expressed by the liver and secreted in the plasma.

DETAILED DESCRIPTION OF THE INVENTION

Definitions

Figure 1:
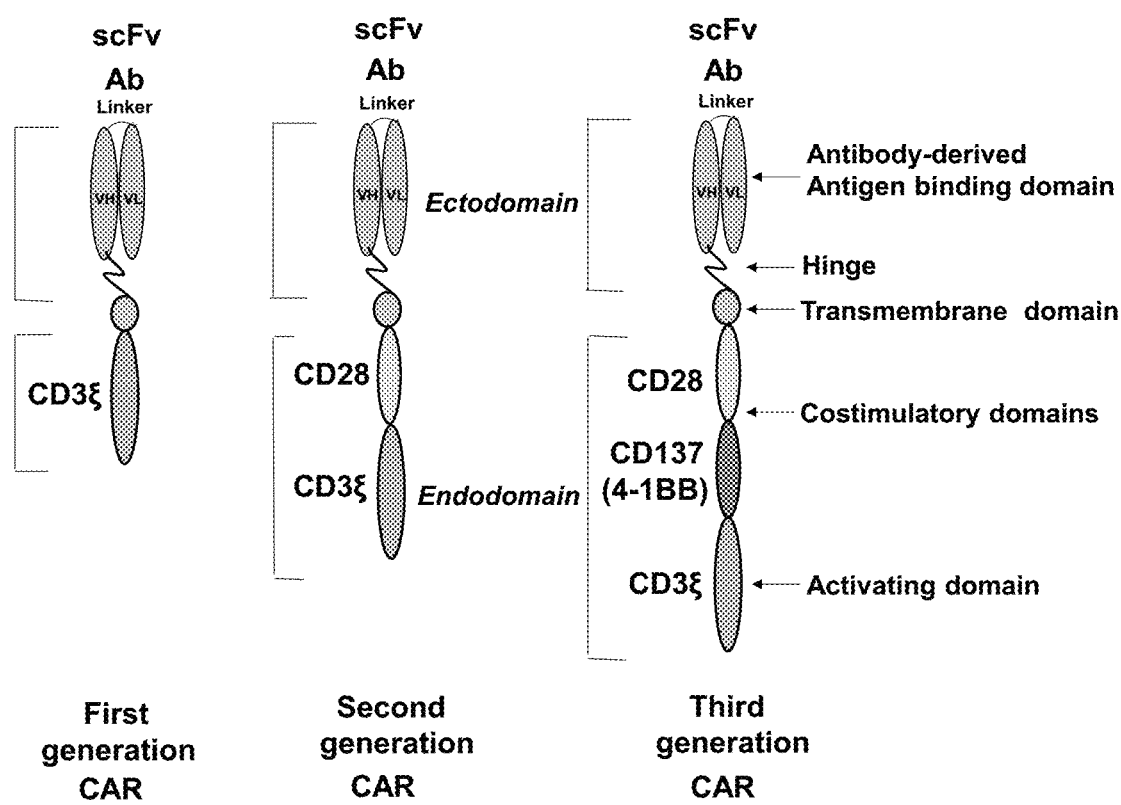
FIG. 1. The structures of first, second, and third generation of CAR. The left panel shows the structure of first generation (no co-stimulation domains), the middle panel shows the second generation (one co-stimulation domain CD28 or 4-BB), and the right panel show the third generation of CAR (two or several co-stimulation domains) [5].

As used herein, a "chimeric antigen receptor (CAR)" means a fused protein containing an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "domain" means one region in a polypeptide which is folded into a particular structure independently of other regions.

As used herein, a transferrin epitope (TF), is a 15 amino acid polypeptide human transferrin motif (epitope for TF antibody binding): having a sequence of K N P D P W A K N L N E K D Y (SEQ ID NO: 1), it is an epitope for binding to transferrin antibody. TF is 564 to 578 amino-acids of human transferrin (protein sequence is available in Uniprot UP02787; uniprot.org/uniprot/P02787. It can be fused to the C-terminus or the N-terminus of a protein, or inserted within an extracellular domain of protein. 2TF, 3TF, 4TF, and 5TF each is a repeat of the 15 amino acid sequence of TF 2-5 times, respectively. 1/2TF is second half of TF, i.e. KNLNEKDY (SEQ ID NO: 2). "A TF sequence", as used herein, includes TF, 1/2TF, and 2-5TF such as 2TF and 3TF.

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv variable regions of immunoglobulin heavy chain (H chain) and light chain (L chain) fragments are linked via a spacer sequence. Various methods for preparing an scFv are known to a person skilled in the art.

As used herein, a "tumor antigen" means a biological molecule having antigenicity, expression of which causes cancer.

The inventors have discovered that adding a TF sequence to the N-terminal or C-terminal of ScFv, or in between $V_H$ and $V_L$. in CAR provides advantages over conventional CAR. The addition of a TF sequence in CAR allows easy detection of CAR-positive cells by using an antibody against transferrin or TF. The addition of TF sequence in CAR also allows to track CAR-T cells in vivo, which can be used for imaging in clinics, and detecting the persistence and longevity of CAR-Tcells. The addition of a TF sequence to CD19-CAR, CD22-CAR and BCMA-CARs leads to safer CAR-T cells with less secretion of cytokines.

The present invention is directed to a chimeric antigen receptor fusion protein comprising from the N-terminus to C-terminus: (i) a single-chain variable fragment (scFv) comprising VH and $V_L$, wherein scFv has an activity against a tumor antigen, (ii) a transmembrane domain, (iii) at least one co-stimulatory domains, and (iv) an activating domain; wherein the fusion protein further comprises a TF sequence (TF, 1/2 TF, or 2-5 TF) either at the N-terminus to ScFv, or between $V_H$ and $V_L$, or at the C-terminus to ScFv, i.e., between $V_L$ or $V_H$ and the transmembrane domain.

In one embodiment, the tumor antigen is selected from the group consisting of: CD19, CD22, BCMA (CD269, TNFRSF17), VEGFR-2, CD4, CD20, CD30, CD25, CD28, CD30, CD33, CD47, CD52, CD56, CD80, CD81, CD86, CD123, CD171, CD276, B7H4, CD133, EGFR, GPC3; PMSA, CD3, CEACAM6, c-Met, EGFRvIII, ErbB2/HER-2, ErbB3/HER3, ErbB4/HER-4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A, mesothelin, NY-ESO-1, PSMA, RANK, ROR1, TNFRSF4, CD40, CD137, TWEAK-R, LTPR, LIFRP, LRP5, MUC1, TCRa, TCRp, TLR7, TLR9, PTCH1, WT-1, Robol, a, Frizzled, OX40, CD79b, and Notch-1-4. In a preferred embodiment, the tumor antigen is CD19, CD22, or BCMA.

In one embodiment, the co-stimulatory domain is selected from the group consisting of CD28, 4-1BB, GITR, ICOS-1, CD27, OX-40 and DAP10. A preferred the co-stimulatory domain is CD28.

A preferred activating domain is CD3 zeta (CD3 Z or CD3ζ)

The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3 zeta chain, CD28, CD3ε, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. Optionally, a short oligopeptide linker or a polypeptide linker, for example, a linker having a length of 2 to 10 amino acids can be arranged between the transmembrane domain and the intracellular domain. In one embodiment, a linker sequence having a glycine-serine continuous sequence can be used.

The insertion of a TF sequence increases functional activities of CAR-T cells to attack tumor cells more effectively and safely.

Figure 2:
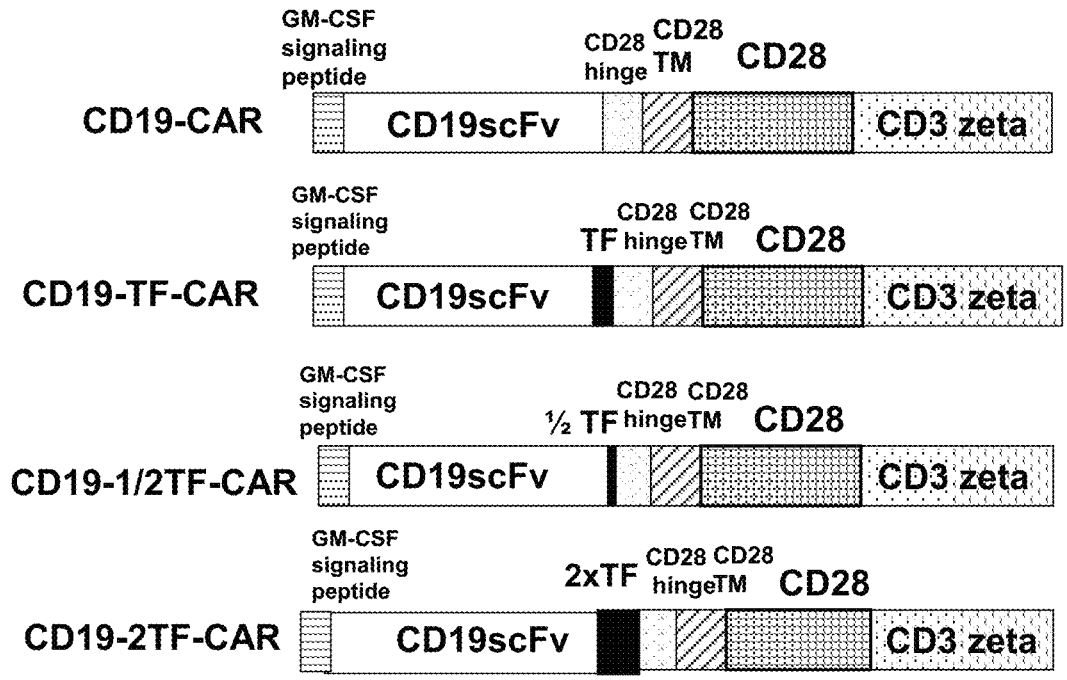
FIG. 2. Structures of CD19-TF-CAR, CD22-TF-CAR and BCMA-TF-CAR. CD19-CAR, CD22-CAR, and BCMA-CAR are shown as controls. GM-CSF is used as a leader sequence for CD19-CAR and CD22 CAR constructs. CD8 leader signaling sequence is used for BCMA-CAR. 1/2 TF; TF or 2xTF are shown at the end of CD19 scFv, CD22 scFv and BCMA scFv, each consisting of a variable fragment of heavy chain; a variable fragment of light chain; and a linker. TM is transmembrane domain; CD28 is CD28 co-activation domain. CD19 scFv has VL-linker-VH structure.
Figure 2:
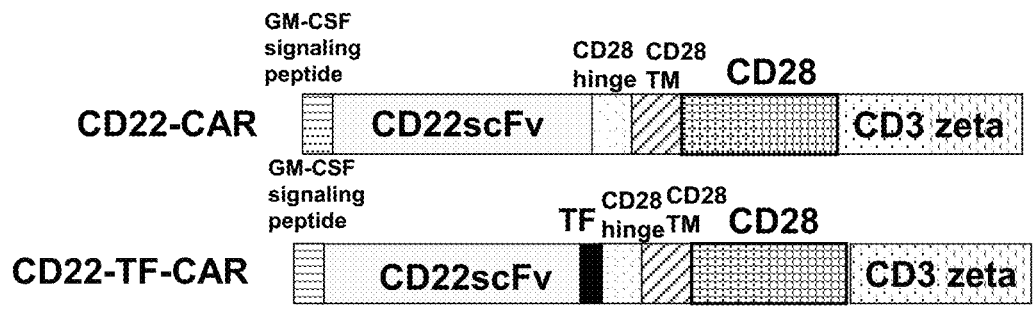
Figure 2:
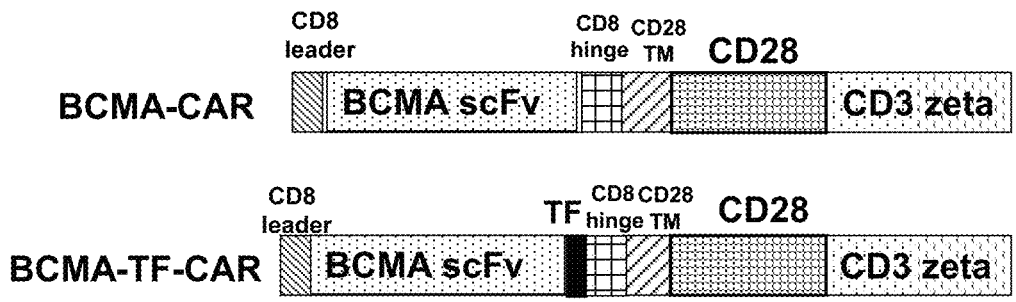

CD19-TF-CAR, CD19-1/2TF-CAR, CD19-2TF-CAR, CD22-TF-CAR, and BCMA-TF-CAR of the present invention are illustrated in FIG. 2 (A-C). ScFv can be VH-linker-VL or VL-linker-VH. In FIG. 2, it is shown that a TF sequence (TF, or 1/2TF, or 2TF) is at the C-terminal end of scFv, however, the TF sequence can also be at the N-terminus of the scFv, or in between VH and VL. The TF epitope sequence should be in the extracellular domain, and not in the intracellular domain so as to be recognized by the anti-TF-antibody.

CD19 and CD22 cell surface antigens are highly expressed in many types of hematologic cancers [2, 6-8]. BCMA is a B-cell maturation antigen (CD269, TNFSR17) that is overexpressed in multiple myeloma (MM) (6). The present invention provides several new constructs. The CD19-TF-CAR construct has similar activity as CD19-CAR. However, CD19-TF-CAR provides advantages over CD19-CAR in clinic, because the presence of TF in CD19-TF-CAR allows the selection of CD19+/−CAR cells during manufacturing with anti-TF antibody-conjugated beads; it also allows to image cells in vivo with a TF antibody. CD22-TF-CAR and BCMA-TF-CAR also have the same advantages for use in clinic as described above for CD19-TF-CAR. BCMA-TF-CAR is useful in treating multiple myeloma. All three constructs (CD19-TF-CAR, CD22-TF-CAR and BCMA-TF-CAR have demonstrated decreased secretion of cytokines, which suggests their increased safety in clinic.

The present invention provides a nucleic acid encoding the TF-containing CARs. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

A nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. A virus vector lacking the replicating ability so as not to self-replicate in an infected cell is preferably used.

For example, when a retrovirus vector is used, a suitable packaging cell based on a LTR sequence and a packaging signal sequence possessed by the vector can be selected for preparing a retrovirus particle using the packaging cell. Examples of the packaging cell include PG13 (ATCC CRL-10686), PA317 (ATCC CRL-9078), GP+E-86 and GP+envAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

A CAR-T cell binds to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

The cell expressing the CAR can be used as a therapeutic agent for a disease. The therapeutic agent comprises the cell expressing the CAR as an active ingredient, and it may further comprise a suitable excipient.

The inventors have generated CD19-TF-CAR-Tcells and CD22-TF-CAR-Tcells against hematologic malignancies (leukemia, lymphoma, and myeloma), which have high killing activity against cancer cells overexpressing CD19 or CD22. The inventors have provided data demonstrating efficient transduction efficiency of T cells transduced with CD19-TF lentiviral construct. The inventors have demonstrated high cytotoxic activity of CD19-TF-CAR-T cells against cancer cells by real-time cytotoxicity assay with cervical cancer cell line Hela stably overexpressing CD19 antigen. The inventors have also demonstrated CD19-TF-CAR-T cells significantly decrease Raji tumor growth in vivo and prolong mouse survival when compared with CD19-Car-T cells. Secretion of cytokines IL-2, and/or IL-6) is significantly less by CD19-TF-CAR-T, CD22-TF-CAR-T, and BCMA-TF-CAR-T cells than by CD19-CAR-T, CD22-CAR-T, and BCMA-CAR-T cells, respectively, against cancer cells.

Inserting a TF sequence of the present invention in CARs does not generate an adverse immune response in humans because the TF sequence is derived from humans. CD19-TF-CAR-Tcells, CD22-TF-CAR-T cells and BCMA-TF-CAR-T cells can be sorted by flow cytometry or by anti-TF antibody-conjugated magnetic beads during manufacturing for enrichment of cytotoxic cells with higher activity. This enrichment approach can be used to generate other CARs for other tumor antigen targets.

The same strategy can be applied to CAR construct using natural killer cells (NK-92 and primary human natural killer cells).

The inventors also developed a new rabbit monoclonal TF-antibody. This antibody can be humanized for use in clinic.

Combination therapy with (i) dual CD19-TF-CAR-T cells and CD22-TF-CAR-T cells, (ii) dual CD19-TF-CAR-T cells and BCMA-TF-CAR-T cells, or (iii) dual BCMA-TF-CAR-T plus other multiple myeloma marker (CS-1, CD138, CD38)-CAR-T, can be used to increase activity of single CAR-T cell-therapy, and can be used safely with less cytokines secretion. The dual CAR-TF-CAR-T cells can be generated with construct with two CARs, or by co-administration of two CARs, or by co-transduction of two CARs.

Combination therapy with bi-specific CD19-CD22-TF-CAR-T, or bi-specific BCMA-plus another ScFv against any of multiple myeloma markers such as CD38, CD319, CD138, CD33-CAR-T cells, can used to increase activity of single CAR-T cell-therapy.

Combination therapy with CD19-TF-CAR and chemotherapy or inhibitors of immune checkpoints (PD-1, CTLA-4 and other) can used to increase activity of single CAR.

Dual or bi-specific CD19/CD22-TF-CAR-Tcells can kill Raji leukemia cell and secrete less cytokines.

Dual or bi-specific-BCMA-TF and multiple myeloma antigen (CD138, CD38, CD319, CD138) CAR-T cells can kill multiple myeloma and secrete less cytokines.

Co-transduction of (i) CD19-TF and CD22-TF lentiviral CAR, or (ii) BCMA and another multiple myeloma antigens, results in generation of CAR-T cells with same or less cytokine secretion against target cancer cells.

The following examples further illustrate the present invention. These examples are intended merely to be illustrative of the present invention and are not to be construed as being limiting.

EXAMPLES

Example 1. CAR Constructs

Mouse FMC63 anti-CD19 scFv (Kochenderfer et al (2009), I. *Immunother*, 32:689-702) was inserted into a second-generation CAR cassette containing a signaling peptide from GM-CSF, a hinge region, transmembrane domain and costimulatory domain from CD28, and the CD3 zeta activation domain; this CAR is herein called the CD19 CAR. The TF sequence (K N P D P W A K N L N E K D Y, SEQ ID NO: 1) was inserted into the CD19 CAR between the scFv and hinge region; this CAR is herein called the CD19-TF CAR.

The VH and VL for CD22 scFv was taken from monoclonal 971 human CD22 Antibody (US Publication No. 20110020344).

Each BCMA scFv was obtained from a BCMA antibody from Promab Technologies (Richmond, Calif.). A "mock" CAR was prepared with an scFv specific for an intracellular protein—and thus a "mock" CAR was not reactive with intact cells.

Example 2. Sequences of CD19-CAR Constructs

Two anti-CD19 ScFv's were used to prepare two CD19-TF-CARs; one from mouse FMC63 anti-CD19 scFv, and another one from humanized clone 11. The sequence of each segment is shown below. Each segment can be replaced with an amino acid sequence having at least 95%, 98%, or 99% identity, wherein the amino acid variation in ScFv is in the framework outside of the CDR regions.
The constructs of CD19-CAR, CD19-TF-CAR, CD19-1/2TF, and DC19-2TF are shown in FIG. 2.

```
1. Mouse FMC 63
<Human GM-CSF Signal peptide>
                                     SEQ ID NO: 3
MLLLVTSLLLCELPHPAFLLIP FMC63 anti-CD19 scFv (VL-Linker-VH)
<VL>
                                     SEQ ID NO: 4
D I Q M T Q T T S S L S A S L G D R V T I S

C R A S Q D I S K Y L N W Y Q Q K P D G T V

K L L I Y H T S R L H S G V P S R F S G S G

S G T D Y S L T I S N L E Q E D I A T Y F C

Q Q G N T L P Y T F G G G T K L E I T

<linker>
                                     SEQ ID NO: 5
G S T S G S G K P G S G E G S T K G <VH>
                                     SEQ ID NO: 6
E V K L Q E S G P G L V A P S Q S L S V T C

T V S G V S L P D Y G V S W I R Q P P R K G

L E W L G V I W G S E T T Y Y N S A L K S R

L T I I K D N S K S Q V F L K Met N S L Q T

D D T A I Y Y C A K H Y Y Y G G S Y A M D Y

W G Q G T S V T V S S
```

In one embodiment as illustrated herein, 3 amino acids AAA are included after VH.

```
<TF sequence> if present, after VH or VL (scFv),
                                     SEQ ID NO: 1
K N P D P W A K N L N E K D Y
The TF sequence was inserted between the scFv and
the CD28 hinge region of the CD19-specific CAR.

<Human CD28 hinge>
                                     SEQ ID NO: 7
I E V M Y P P P Y L D N E K S N G T I I

H V K G K H L C P S P L F P G P S K P

<Transmembrane Domain TM28>
                                     SEQ ID NO: 8
F W V L V V V G G V L A C Y S L L V T

V A F I I F W V

<Co-stimulating domain human CD28>
                                     SEQ ID NO: 9
R S K R S R L L H S D Y M N M T P R R P G

P T R K H Y Q P Y A P P R D F A A Y R S

<Activation domain human CD3-zeta>
                                     SEQ ID NO: 10
R V K F S R S A D A P A Y Q Q G Q N Q L Y

N E L N L G R R E E Y D V L D K R R G R D

P E M G G K P R R K N P Q E G L Y N E L Q

K D K M A E A Y S E I G M K G E R R R G K
```

CD19-TF-CAR sequence with mouse FMC 63 scFv can be shown as SEQ ID NO: 11, TF is bold and underlined, CD19scFV is in Italic font:

M L L L V T S L L L C E L P H P A F L L I P *D I Q*

*M T O T T S S L S A S L G D R V T I S C R A S O D*

*I S K Y L N W Y Q Q K P D G T V K L L I Y H T S R*

*L H S G V P S R F S G S G S G T D Y S L T I S N L*

*E Q E D I A T Y F C Q O G N T L P Y T F G G G T K*

*L E I T G S T S G S G K P G S G E G S T K G E V K*

*L Q E S G P G L V A P S O S L S V T C T V S G V S*

*L P D Y G V S W I R Q P P R K G L E W L G V I W G*

-continued

```
S E T T Y Y N S A L K S R L T I I K D N S K S Q V
F L K M N S L Q T D D T A I Y Y C A K H Y Y Y G G
S Y A M D Y W G Q G T S V T V S S A A A KNPDP
WAKNLNEKDY I E V M Y P P P Y L D N E K S
N G T I I H V K G K H L C P S P L F P G P S K P F
W V L V V V G G V L A C Y S L L V T V A F I I F W
V R S K R S R L L H S D Y M N M T P R R P G P T R
K H Y Q P Y A P P R D F A A Y R S R V K F S R S A
D A P A Y Q Q G Q N Q L Y N E L N L G R R E E Y D
V L D K R R G R D P E M G G K P R R K N P Q E G L
Y N E L Q K D K M A E A Y S E I G M K G E R R R G
K G H D G L Y Q G L S T A T K D T Y D A L H M Q A
L P P R
```

In one embodiment, 8 amino-acid of TF (1/2 TF) was used.

```
<1/2 TF SEQUENCE>
                                    SEQ ID NO 2
KNLNEKDY,

<CD 19-1/2TF-CAR>,

1/2TF sequence is shown in bold, underlined.
                                    SEQ ID NO:12
M L L L V T S L L L C E L P H P A F L L I P D I Q
M T Q T T S S L S A S L G D R V T I S C R A S Q D
I S K Y L N W Y Q Q K P D G T V K L L I Y H T S R
L H S G V P S R F S G S G S G T D Y S L T I S N L
E Q E D I A T Y F C Q Q G N T L P Y T F G G G T K
L E I T G S T S G S G K P G S G E G S T K G E V K
L Q E S G P G L V A P S Q S L S V T C T V S G V S
L P D Y G V S W I R Q P P R K G L E W L G V I W G
S E T T Y Y N S A L K S R L T I I K D N S K S Q V
F L K M N S L Q T D D T A I Y Y C A K H Y Y Y G G
S Y A M D Y W G Q G T S V T V S S A A A KNLNE
KDY I E V M Y P P P Y L D N E K S N G T I I H V
K G K H L C P S P L F P G P S K P F W V L V V V G
G V L A C Y S L L V T V A F I I F W V R S K R S R
L L H S D Y M N M T P R R P G P T R K H Y Q P Y A
P P R D F A A Y R S R V K F S R S A D A P A Y Q Q
G Q N Q L Y N E L N L G R R E E Y D V L D K R R G
R D P E M G G K P R R K N P Q E G L Y N E L Q K D
K M A E A Y S E I G M K G E R R R G K G H D G L Y
Q G L S T A T K D T Y D A L H M Q A L P P R
```

In one embodiment, 2 TF was used,
CD19-2TF-CAR was generated with two TF sequences after CD19 ScFv; its sequence is shown below. Two TF sequences are marked bold and underlined.

```
                                    (SEQ ID NO: 13)
M L L L V T S L L L C E L P H P A F L L I P D I Q
M T Q T T S S L S A S L G D R V T I S C R A S Q D
I S K Y L N W Y Q Q K P D G T V K L L I Y H T S R
L H S G V P S R F S G S G S G T D Y S L T I S N L
E Q E D I A T Y F C Q Q G N T L P Y T F G G G T K
L E I T G S T S G S G K P G S G E G S T K G E V K
L Q E S G P G L V A P S Q S L S V T C T V S G V S
L P D Y G V S W I R Q P P R K G L E W L G V I W G
S E T T Y Y N S A L K S R L T I I K D N S K S Q V
F L K M N S L Q T D D T A I Y Y C A K H Y Y Y G G
S Y A M D Y W G Q G T S V T V S S A A A KNPDP
WAKNLNEKDYKNPDPWAKNLNEKDY
I E V M Y P P P Y L D N E K S N G T I I H V K G K
H L C P S P L F P G P S K P F W V L V V V G G V L
A C Y S L L V T V A F I I F W V R S K R S R L L H
S D Y M N M T P R R P G P T R K H Y Q P Y A P P R
D F A A Y R S R V K F S R S A D A P A Y Q Q G Q N
Q L Y N E L N L G R R E E Y D V L D K R R G R D P
E M G G K P R R K N P Q E G L Y N E L Q K D K M A
E A Y S E I G M K G E R R R G K G H D G L Y Q G L
S T A T K D T Y D A L H M Q A L P P R
```

2. CD19 Humanized-Clone 11

Clone 11 ScFv (VL-linker-VH) was used to generated CD19-TF-CAR.

The VL, VH, and linker sequences are shown below. The CDR regions are bolded.

```
<VL>
                                    SEQ ID NO: 14
DIQNITQSPSSLSASVGDRVTITCRASQDISKYLNWYQQKPGKAYK

LLIYHTSRLHSGVPSRFSGSGSGTDFTLTISSLQPEDFATYYCQQG

NTLPYTFGGGTKVEIK

<VH>
                                    SEQ ID NO: 16
QVQLQESGPGLVKPSETLSLTCTVSGGSLPDYGVSWIRQPPGKGL

EWIGVIWGSETTYYNSALKSRVTISVDTSKNQFSLKLSSVTAADTA

VYYCAKHYYYGGSYAMDYWGQGTLVTVSS
```

<Linker> SEQ ID NO: 15
CD19-TF-CAR containing humanized-clone 11, ScFv was prepared; the CAR sequence is similar to SEQ ID NO: 11 except VL and VH.

Example 3. Sequences of CD22-CAR Construct

The CD22-TF-CAR is shown in FIG. 2. Human CD22 m971 scFV was used to generate CD22-TF CAR sequence. The sequence of each segment is shown below. Each segment can be replaced with an amino acid sequence having at least 95%, 98%, or 99% identity, wherein the amino acid variation in ScFv is in the framework outside of the CDR regions.

Human GM-CSF Signal peptide (see Example 2) was used in the CAR construct.

<CD22 VH>
SEQ ID NO: 17
Q V Q L Q Q S G P G L V K P S Q T L S L T C A I

S G D S V S S N S A A W N W I R Q S P S R G L E

W L G R T Y Y R S K W Y N D Y A V S V K S R I T

I N P D T S K N Q F S L Q L N S V T P E D T A V

Y Y C A R E V T G D L E D A F D I W G Q G T M V

T V S S

<CD22 VL>
SEQ ID NO: 18
D I Q M T Q S P S S L S A S V G D R V T I T C R

A S Q T I W S Y L N W Y Q Q R P G K A P N L L I

Y A A S S L Q S G V P S R F S G R G S G T D F T

L T I S S L Q A E D F A T Y Y C Q Q S Y S I P Q

T F G Q G T K L E I K

The sequence of CD22-TF-CAR is shown below. CD22 ScFv containing VH-linker-VL is shown by Italic font. Linker is GGGGSGGGGSGGGGS (SEQ ID NO:19)

TF is shown bold and underlined.

(SEQ ID NO: 20)
M L L L V T S L L L C E L P H P A F L L I P Q V

Q L Q Q S G P G L V K P S Q T L S L T C A I S G

D S V S S N S A A W N W I R Q S P S R G L E W L

G R T Y Y R S K W Y N D Y A V S V K S R I T I N

P D T S K N Q F S L Q L N S V T P E D T A V Y Y

C A R E V T G D L E D A F D I W G Q G T M V T V

S S G G G G S G G G G S G G G G S D I Q M T Q S

P S S L S A S V G D R V T I T C R A S Q T I W S

Y L N W Y Q Q R P G K A P N L L I Y A A S S L Q

S G V P S R F S G R G S G T D F T L T I S S L Q

A E D F A T Y Y C Q Q S Y S I P Q T F G Q G T K

L E I K K N P D W A K N L N E K D Y I E V M Y

P P P Y L D N E K S N G T I I H V K G K H L C P

S P L F P G P S K P F W V L V V V G G V L A C Y

S L L V T V A F I I F W V R S K R S R L L H S D

Y M N M T P R R P G P T R K H Y Q P Y A P P R D

F A A Y R S R V K F S R S A D A P A Y Q Q G Q N

Q L Y N E L N L G R R E E Y D V L D K R R G R D

P E M G G K P R R K N P Q E G L Y N E L Q K D K

M A E A Y S E I G M K G E R R R G K G H D G L Y

Q G L S T A T K D T Y D A L H M Q A L P P R

Example 4. Sequences of BCMA-CAR Constructs

The construct of BCMA-TF-CAR is shown in FIG. 2.

Four ScFv's were used to prepare CAR; one from Clone A (mouse), one from Clone B (mouse), one from Clone 7 (humanized), and one from Clone 7B5B4 (humanized). The sequence of each segment is shown below. Each segment can be replaced with and amino acid sequence having at least 95%, 98%, or 99% identity, wherein the amino acid variation in ScFv is in the framework outside of the CDR regions.

1. BCMA-Clone A

Human CD8 leader signaling sequence is used for BCMA-CAR.

<CD8 leader signaling sequence>:
SEQ ID NO: 21
M A L P V T A L L L P L A L L L H A A R P In between the CD8 leader sequence and ScFv sequence, there are two amino acids AS connecting leader and ScFv, this is enzyme (Nhe I) site flanking scFv from 5' end BCMA Clone A (Promab Biotechnologies) ScFv was used to generate BCMA-TF CAR.
<BCMA VH, Clone A>
SEQ ID NO: 22
Q V Q V V E S G G G L V K P G G S L K L S C V V S

G F A F S S Y D M S W V R Q T P E K R L E W V A Y

I N S G G Y I T Y Y L D T V K G R F T I S R D N A

K N I L Y L Q M N S L K S E D S A L Y Y C V P G F

A H W G Q G T L V I V S

<Linker>
SEQ ID NO: 19
GGGGSGGGGSGGGGS

<BCMA, Clone A VL>
SEQ ID NO: 23
D I V M T Q A A P S V P V T P G E S V S I S C R

S N K S L L H S N G N T Y L Y W F L Q R P G Q S

P Q L L I Y R M S N L A S G V P D R F S G S G S

G T A F T L R I S R V E A E D V G V Y Y C M Q H

L E Y P Y T F G G G T K L E I K

In between the TF sequence and CD8 hinge sequence, there are two amino acids LE, this is enzyme (Xho I) site flanking scFv from 3' end.

<Human CD8 hinge>
SEQ ID NO: 24
K P T T T P A P R P P T P A P T I A S Q P L S L R

P E A S R P A A G G A V H T R G L D F A S D K P

The sequence of BCMA-TF-CAR (Clone A) is shown below. TF is bold and underlined, BCMA ScFv containing VH-linker-VL is shown by Italic. The CAR contains CD8 leader sequence that is shown by Italic underlined and CD8 hinge sequence underlined.

(SEQ ID NO: 25)
*<u>M A L P V T A L L L P L A L L L H A A R P</u> A*
*S Q V Q V V E S G G G L V K P G G S L K L S*
*C V V S G F A F S S Y D M S W V R Q T P E K*
*R L E W V A Y I N S G G Y I T Y Y L D T V K*
*G R F T I S R D N A K N I L Y L Q M N S L K*
*S E D S A L Y Y C V P G F A H W G Q G T L V*
*I V S G G G G S G G G G S G G G G S D I V M*
*T Q A A P S V P V T P G E S V S I S C R S N*
*K S L L H S N G N T Y L Y W F L Q R P G Q S*
*P Q L L I Y R M S N L A S G V P D R F S G S*
*G S G T A F T L R I S R V E A E D V G V Y Y*
*C M Q H L E Y P Y T F G G G T K L E I K* K N
P D P W A K N L N E K D Y L E <u>K P T T T P A</u>
<u>P R P P T P A P T I A S Q P L S L R P E A S</u>
<u>R P A A G G A V H T R G L D F A S D K P</u> F W
V L V V V G G V L A C Y S L L V T V A F I I
F W V R S K R S R L L H S D Y M N M T P R R
P G P T R K H Y Q P Y A P P R D F A A Y R S
R V K F S R S A D A P A Y Q Q G Q N Q L Y N
E L N L G R R E E Y D V L D K R R G R D P E
M G G K P Q R R K N P Q E G L Y N E L Q K D
K M A E A Y S E I G M K G E R R R G K G H D
G L Y Q G L S T A T K D T Y D A L H M Q A L
P P R

2. BCMA-Clone B
BCMA clone B (Promab Biotechnologies) ScFv was used to generate BCMA-TF CAR.
<VH, Clone B>,
SEQ ID NO: 26
*Q V Q V V E S G G G L M K P G G S L K L S C*
*V V S G F A F S S Y D M S W V R Q T P E K R*
*L E W V A Y I N S G G Y I T Y Y L D T V K G*
*R F T I S R D N A K K S L Y L Q M N S L K S*
*E D S A L Y Y C V P G F A H W G Q G T L V I*
*V S*

<VL, Clone B>,
SEQ ID NO: 27
*D V V M T Q T P L S L P V S L G D Q A S I S*
*C R S S Q S L V H R N G N S Y L H W Y L Q R*
*P G Q S P K L L I Y K V S S R F S G V P D R*
*F S G S G S G T D F T L K I R R V E A E D L*
*G V Y F C S Q S T H F P Y T F G G G T M L E*
*I K*

The sequence of BCMA-TF-CAR (Clone B) is shown below; the CAR sequence is similar to SEQ ID NO: 25 except VH and VL. TF is bold and underlined, BCMA ScFv containing VH-linker-VL is shown by Italic. The CAR contained CD8 leader sequence that is shown by italic underlined and CD8 hinge sequence underlined.

(SEQ ID NO: 28)
*<u>M A L P V T A L L L P L A L L L H A A R P</u> A S Q*
*V Q V V E S G G G L V K P G G S L K L S C V V S*
*G F A F S S Y D M S W V R Q T P E K R L E W V A*
*Y I N S G G Y I T Y Y L D T V K G R F T I S R D*
*N A K N I L Y L Q M N S L K S E D S A L Y Y C V*
*P G F A H W G Q G T L V I V S G G G G S G G G G*
*S G G G G S D V V M T Q T P L S L P V S L G D Q*
*A S I S C R S S Q S L V H R N G N S Y L H W Y L*
*Q R P G Q S P K L L I Y K V S S R F S G V P D R*
*F S G S G S G T D F T L K I R R V E A E D L G V*
*Y F C S Q S T H F P Y T F G G G T M L E I K* K N
P D P W A K N L N E K D Y L E <u>K P T T T P A P R</u>
<u>P P T P A P T I A S Q P L S L R P E A S R P A A</u>
<u>G G A V H T R G L D F A S D K P</u> F W V L V V V G
G V L A C Y S L L V T V A F I I F W V R S K R S
R L L H S D Y M N M T P R R P G P T R K H Y Q P
Y A P P R D F A A Y R S R V K F S R S A D A P A
Y Q Q G Q N Q L Y N E L N L G R R E E Y D V L D
K R R G R D P E M G G K P Q R R K N P Q E G L Y
N E L Q K D K M A E A Y S E I G M K G E R R R G
K G H D G L Y Q G L S T A T K D T Y D A L H M Q
A L P P R

3. BCMA-Clone 7
<VH, Clone 7>,
SEQ ID NO: 29
Q L Q Q S G P E L V K S G A S V K M S C K A S G
Y T F T S Y V M H W V K Q K P G Q G L E W I G F
I I P Y N D D T K Y N E K F K G K A S L T S D K
S S S T A F M E L S S L T S E D S A V Y Y C A R
W N Y D G Y F D V W G A G T T V T V S S <VL, Cone 7>
SEQ ID NO: 30
<u>D V V M T Q T P L S L P V S L G D Q A S I S C R</u>
<u>S S Q S L V H S N G N T Y L H W Y L Q K P G Q S</u>

-continued
P K L L I Y K V S N R F S G V P D R F S G S G S

G T D F T L K I S R V E A E D L G V Y F C S Q I

T H V P Y T F G G G T K L E I R R

BCMA-TF CAR containing Clone 7, Scfv (VH-linker-VL) was prepared; the CAR sequence is similar to SEQ ID NO: 28 except VH and VL.

4. BCMA scFv (clone 7B5B4)
<VH, Clone 7B5B4>,
SEQ ID NO: 31
Q L Q Q S G P E L V K S G A S V K M S C K A S G

Y T F T S Y V M H W V K Q K P G Q G L E W I G F

I I P Y N D D T K Y N E K F K G K A S L T S D K

S S S T A Y M E L S S L T S E D S A V Y Y C A R

W D F D G Y F D V W G A G T T V T V S S

<VL, Clone 7B5B4>,
SEQ ID NO: 32
D V V M T Q T P L S L P V S L G D Q A S I S C R

S S Q S L V H S N G N T Y L H W Y L Q K P G Q S

P K L L I Y K V S N R F S G V P D R F S G S G S

G T D F T L K I S R V E A E D L G V Y F C S Q I

T H V P Y T F G G G T K L E I R R

BCMA-TF CAR containing Clone 7B5B4, ScFv (VH-linker-VL) was prepared; the CAR sequence is similar to SEQ ID NO: 28 except and VL, Example 5. Generation of CAR-Encoding Lentivirus DNAs encoding the CARs (Examples 2-4) were synthesized and subcloned into a third-generation lentiviral vector with EF1a promoter by Syno Biological (Beijing, China). All CAR lentiviral constructs were sequenced in both directions to confirm CAR sequence and used for lentivirus production. Ten million growth-arrested HEK293FT cells (Thermo Fisher) were seeded into T75 flasks and cultured overnight, then transfected with the pPACKH1 Lentivector Packaging mix (System Biosciences, Palo Alto, Calif.) and 10 μg of each lentiviral vector using the CalPhos Transfection Kit (Takara, Mountain View, Calif.). The next day the medium was replaced with fresh medium, and 48 h later the lentivirus-containing medium was collected. The medium was cleared of cell debris by centrifugation at 2100 g for 30 min. The virus particles were collected by centrifugation at 112,000 g for 100 min, suspended in AIM V medium, aliquoted and frozen at −80° C. The titers of the virus preparations were determined by quantitative RT-PCR using the Lenti-X qRT-PCR kit (Takara) according to the manufacturer's protocol and the 7900HT thermal cycler (Thermo Fisher). The lentiviral titers were >1×10$^8$ pfu/ml.

Example 6. Generation and Expansion of CAR-T Cells

PBMC were suspended at 1×10$^6$ cells/ml in AIM V-AlbuMAX medium (Thermo Fisher) containing 10% FBS and 300 U/ml IL-2 (Thermo Fisher), mixed with an equal number (1:1 ratio) of CD3/CD28 Dynabeads (Thermo Fisher), and cultured in non-treated 24-well plates (0.5 ml per well). At 24 and 48 hours, lentivirus was added to the cultures at a multiplicity of infection (MOI) of 5, along with 1 μl of TransPlus transduction enhancer (AlStem). As the T cells proliferated over the next two weeks, the cells were counted every 2-3 days and fresh medium with 300 U/ml IL-2 was added to the cultures to maintain the cell density at 1-3×10$^6$ cells/ml.

Example 7. Flow Cytometry

To measure CAR expression, 0.5 million cells were suspended in 100 μl of buffer (PBS containing 0.5% BSA) and incubated on ice with 1 μl of human serum (Jackson Immunoresearch, West Grove, Pa.) for 10 min. Then 1 μl of allophycocyanin (APC)-labeled anti-CD3 (eBioscience, San Diego, Calif.), and 2 μl of either phycoerythrin (PE)-labeled anti-TF or its isotype control antibody was added, and the cells were incubated on ice for 30 min. The cells were rinsed with 3 ml of buffer, then suspended in buffer and acquired on a FACSCalibur (BD Biosciences). Cells were analyzed for CD3 staining versus TF staining or isotype control staining.

Example 8. Generation of the Stable HeLa-CD19 Cell Line

To generate HeLa cells stably expressing human CD19, a DNA encoding the human CD19 open reading frame was synthesized and subcloned into the pCD510 lentiviral vector (System Biosciences) by Syno Biological. Lentivirus containing the vector was made as described above. HeLa cells were infected with the lentivirus at an MOI of 5 and cultured in the presence of 1 μg/ml puromycin to generate resistant cells, herein called HeLa-CD19. The expression of CD19 was confirmed by flow cytometry with a CD19 antibody (BioLegend).

Example 9. Real-Time Cytotoxicity Assay (RTCA)

Adherent target cells (HeLa or HeLa-CD19) were seeded into 96-well E-plates (Acea Biosciences, San Diego, Calif.) at 1×10$^4$ cells per well and monitored in culture overnight with the impedance-based real-time cell analysis (RTCA) iCELLigence system (Acea Biosciences). The next day, the medium was removed and replaced with AIM V-AlbuMAX medium containing 10% FBS±1×10$^5$ effector cells (CAR-T cells or non-transduced T cells), in triplicate. The cells in the E-plates were monitored for another 2-3 days with the RTCA system, and impedance was plotted over time. Cytolysis was calculated as (impedance of target cells without effector cells—impedance of target cells with effector cells)×100/impedance of target cells without effector cells. For non-adherent target cells (Raji), the E-plates were first coated with an anti-CD40 antibody (Acea Biosciences) to bind to the CD40$^+$ Raji cells. Then 1×10$^4$ Raji cells were plated per well and the RTCA assay was performed as described above.

Example 10. Cytokine Secretion Assay

The target cells (Raji or HeLa-CD19) were cultured with the effector cells (CAR-T cells or non-transduced T cells) at a 1:1 ratio (1×10$^4$ cells each) in U-bottom 96-well plates with 200 μl of AIM V-AlbuMAX medium containing 10% FBS, in triplicate. After 16 h the top 150 μl of medium was transferred to V-bottom 96-well plates and centrifuged at 300 g for 5 min to pellet any residual cells. The top 120 µl of supernatant was transferred to a new 96-well plate and analyzed by ELISA for human IFN-γ and IL-2 levels using kits from Thermo Fisher according to the manufacturer's protocol.

Example 11. Statistical Analysis

Data were analyzed and plotted with Prism software (GraphPad, San Diego, Calif.). Comparisons between two groups were performed by unpaired Student's t test. $p<0.05$ was considered significant.

Example 12. Flow Cytometry with New Promab's Rabbit TF Antibody Shows Efficient Transduction of T Cells with CD19-CAR or CD22 Lentiviruses and Expression CD19 or CD22-TF-ScFv Promab Biotechnologies developed several TF antibodies that were generated against the 15 amino-acid peptide SEQ ID NO: 1.
The TF peptide sequence was conjugated to carrier KLH (Keyhole limpet Hemocyanin) protein to more effectively immunize rabbits, The best clones were selected by ELISA. PBMC was collected from rabbits and used for cloning and library generation. The monoclonal TF antibody was generated by yeast display and FACS analysis with labeled 15 amino-acid peptide.

Example 13. TF Antibody Detects TF Epitope Sequence Inside CAR

Figure 3:
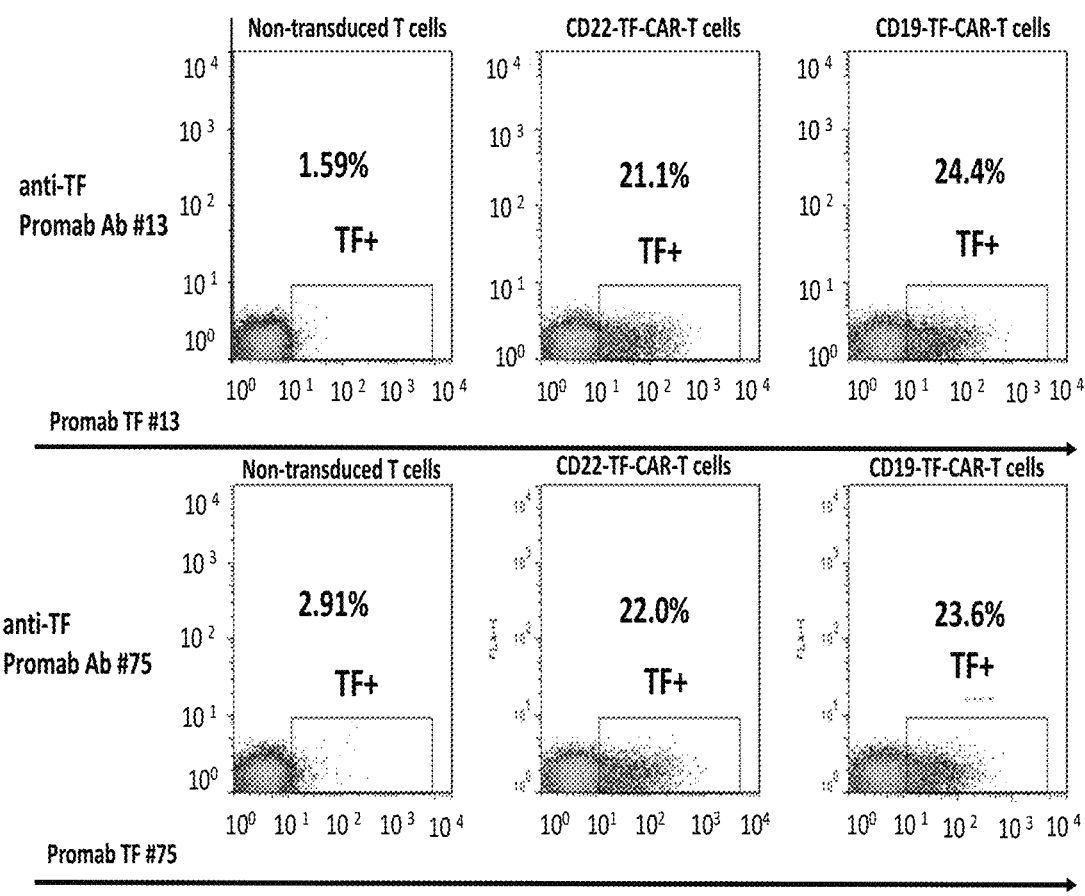
FIG. 3. TF antibodies generated against 15 amino-acid TF epitope detect CD19-TF and CD22-TF-CAR. FACS analysis with TF-PE antibody (X-axis) and CD3-APC antibody as described in Example 5 (Y-axis) is shown. >20% of CD19 and CD22-TF-CAR-T cells are TF+ positive at 14 days of expansion.

The best TF clones (Ab #13 and #75) were used for FACS analysis with CD19-TF and CD22-TF-CAR-T cells (FIG. 3). The FACS was done as described in Example 5. CD19-TF and CD22-TF CAR-T cells were effectively detected with two different rabbit monoclonal TF antibodies (FIG. 3). The staining with TF antibody was much better than with Fab antibody (not shown). Thus, TF-antibodies can be used in clinic for sorting and imaging of TF-positive CAR-T cells.

Figure 4:
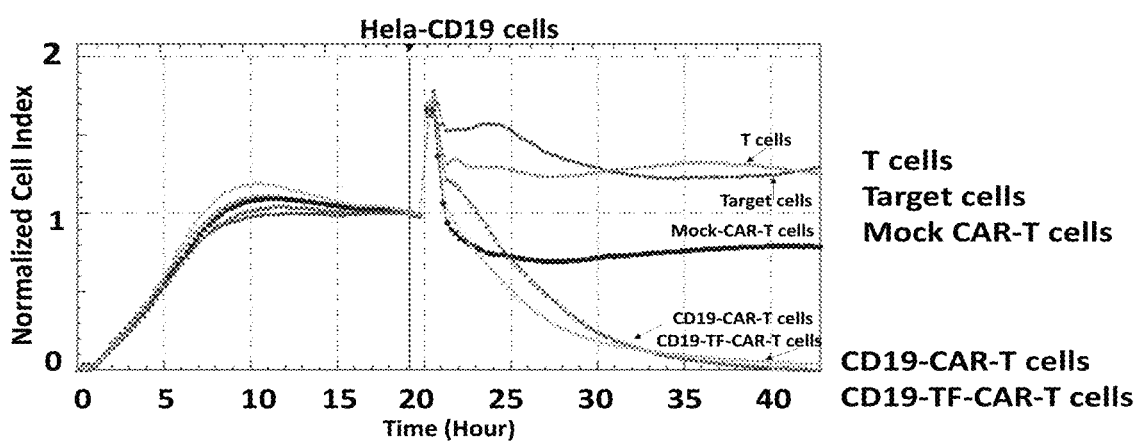
FIG. 4. Real-time cytotoxicity assay (RTCA) with CD19-positive Hela cervical cancer cells. RTCA plot. 10:1 ratio of Effector to Target cells was used. T cells, Mock-CAR-T cells were used as negative control cells against Hela-CD19-posirive cells. The CD19-TF and CD19-CAR-T cells effectively killed Hela-CD19-posirive cells.

Example 14. CD19-TF-CAR-T Cells Demonstrate High Cytotoxicity Against CD19-Positive Hela-CD19 Cells The Real-time highly sensitive cytotoxicity assay demonstrated high activity of CD19-TF-CAR-T cells against CD19-positive Hela cells (FIG. 4). CD19-TF specifically killed Hela-CD19-positivel cells as well as CD19-CAR-T cells. CD22 and CD22-TF specifically killed Hela-CD22 target cells (not shown).

Figure 5:
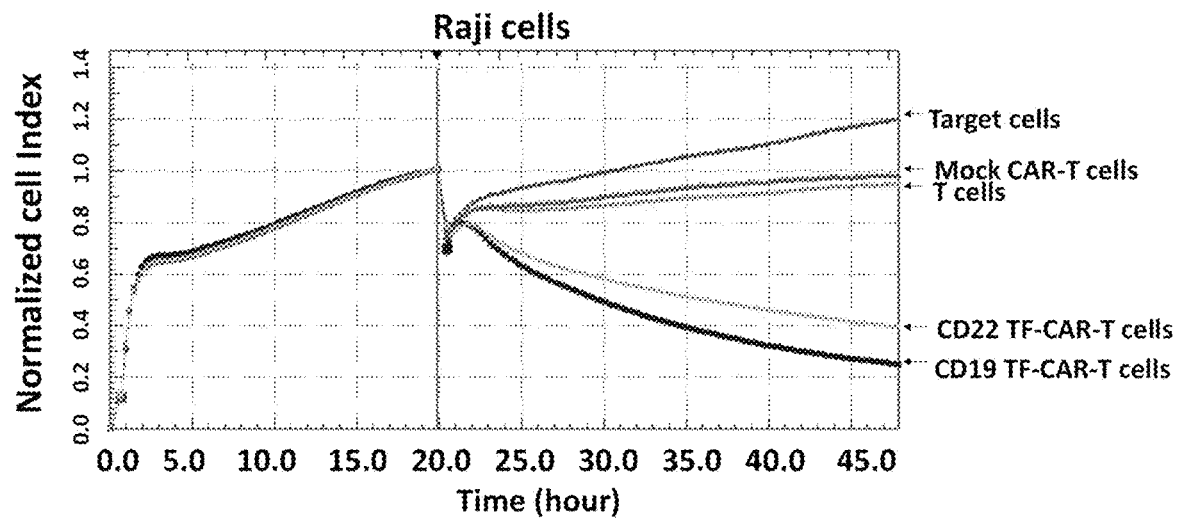
FIG. 5. Real-time cytotoxicity assay with CD19-positive and CD22-positive Raji lymphoma cells. The RTCA assay showed high cytotoxic activity of CD19-TF and CD22-TF-CAR-T cells against Raji cells.

Example 15. CD19-TF-CAR-T Cells and CD22-TF-CAR-T Cells Killed Raji (CD19-Positive and CD22-Positive) Lymphoma Cells This experiment demonstrates the high cytotoxic activity of CD19-TF-CAR-T cells against Raji lymphoma cancer cells that are positive for CD19 and CD22 antigen (FIG. 5). CD19-TF CAR-T were highly cytotoxic against Raji cells with endogenous expression of CD19 (FIG. 5). No significant differences in activity was observed between CD19-TF and CD19-CAR-T cells in Raji cells (not shown).

Figure 6:
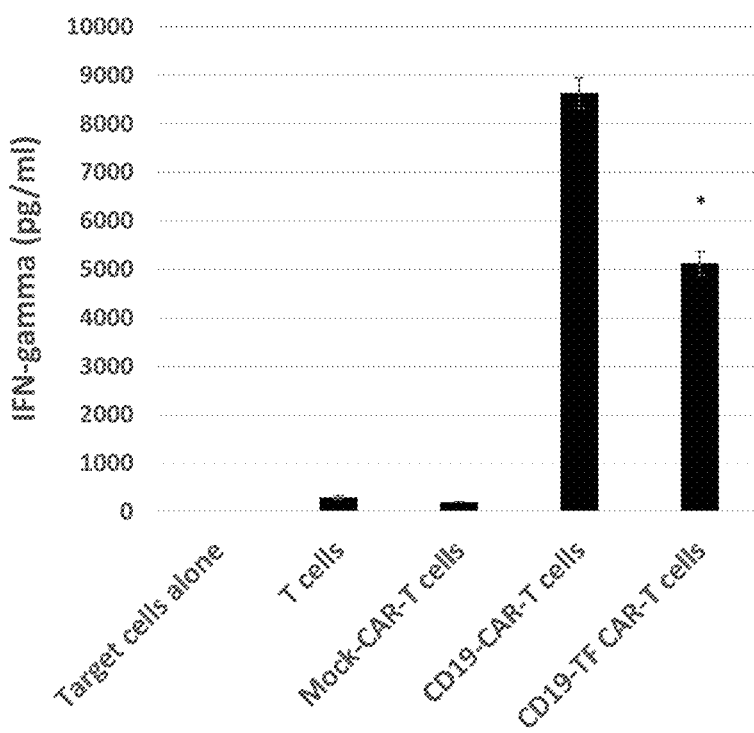
FIG. 6. Secretion of IFN-gamma by CD19-TF-CAR-T cells is significantly less than by CD19 CAR-T cells against Raji cells. E:T (effector cells: Target cells) ratio was 10:1. *p<0.01 CD19-TF versus CD19-CAR-T cells. The level of secretion of cytokines was normalized to the level of CAR-expression.

Example 16. CD19-TF-CAR Secrets Significantly Less IFN-Gamma than CD19-CAR-T Cells We performed ELISA assay for IFN-gamma secretion by CD19 and CD19-TF-CAR-T cells against Raji cells (FIG. 6). CD19-TF CAR-T cells secreted significantly less IFN-gamma than CD19-CAR-T cells (FIG. 6). Decreased secretion of IFN-gamma by CD19-TF cells versus CD19-CAR-T cells was also observed in Hela-CD19 cells (it was equal to 6128 pg/ml by CD19-TF cells; and 8868.3 pg/ml by CD19-CAR-T cells).

Figure 7:
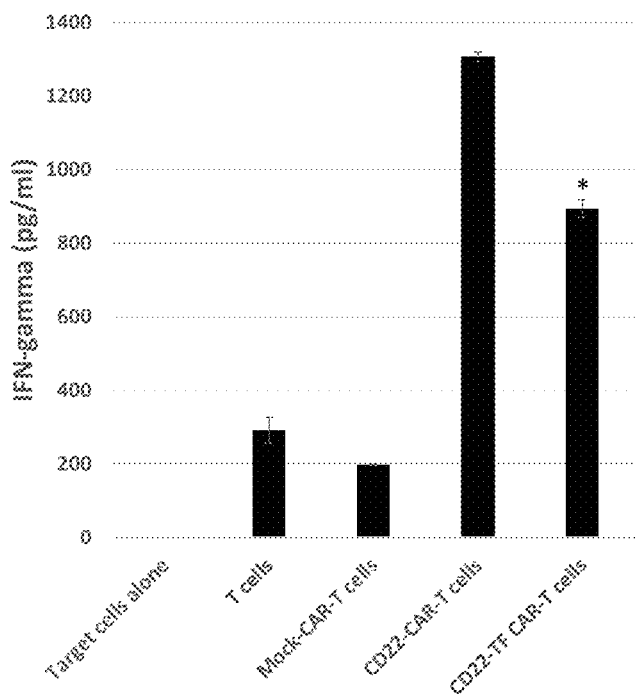
FIG. 7. Secretion of IFN-gamma by C CD22-TF-CAR-T cells is significantly less than by CD22-CAR-T cells against Raji cells. *p<0.01, CD22-TF versus CD22-CAR-T cells. The level of secretion of cytokines was normalized to the level of CAR-expression.

Example 17. CD22-TF-CAR Secretes Significantly Less IFN-Gamma than CD22-CAR-T Cells The level of IFN-gamma secreted by CD22-TF was significantly less than by CD22-CAR-T cells against target Raji cells (FIG. 7)

Figure 8:
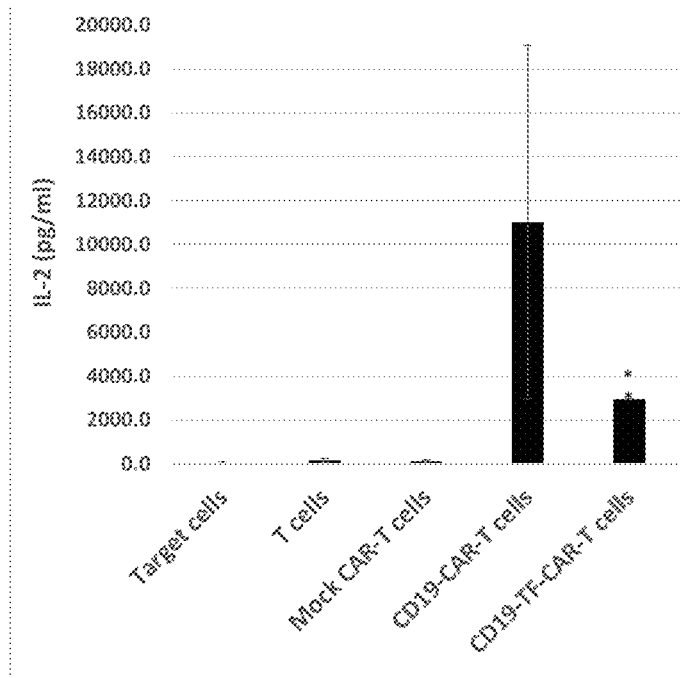
FIG. 8. Secretion of IL-2 by CD19-TF-CAR-T cells is less than by CD19 CAR-T cells against Raji cells. E:T ratio was 10:1. The level of secretion of cytokines was normalized to the level of CAR-expression.
Figure 9:
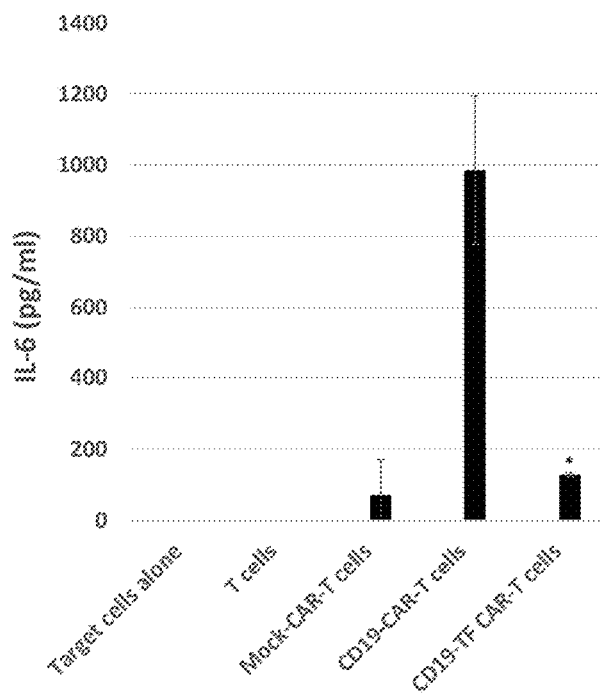
FIG. 9. Secretion of IL-6 by CD19-TF-CAR-T cells is significantly less than by CD19 CAR-T cells against Raji cells. E:T ratio was 10:1. The level of secretion of cytokines was normalized to the level of CAR-expression. *p<0.02, CD19-TF versus CD19-CAR-T cells. The level of secretion of cytokines was normalized to the level of CAR-expression FIG. 10. CD19-1/2TF and CD19-2TF-CAR have same cytotoxic activity as CD19-CAR against target Hela-CD19 cells. RTCA assay was used with target cells (E:T=10:1). N=3, average plus standard deviations are shown.

Example 18. CD19-TF Secrete Less IL-2 and IL-6 than CD19-CAR-T Cells Against Raji cells The decreased secretion of IL-2 (FIG. 8) and IL-6 (FIG. 9) by CD19-TF-CAR-T cells versus CD19-CAR-T cells was observed in Raji cells. CD22-CAR-T and CD22-TF-CAR-T cells secreted very low levels of IL-2 and IL-6 in Raji cells (not shown).

Figure 10:
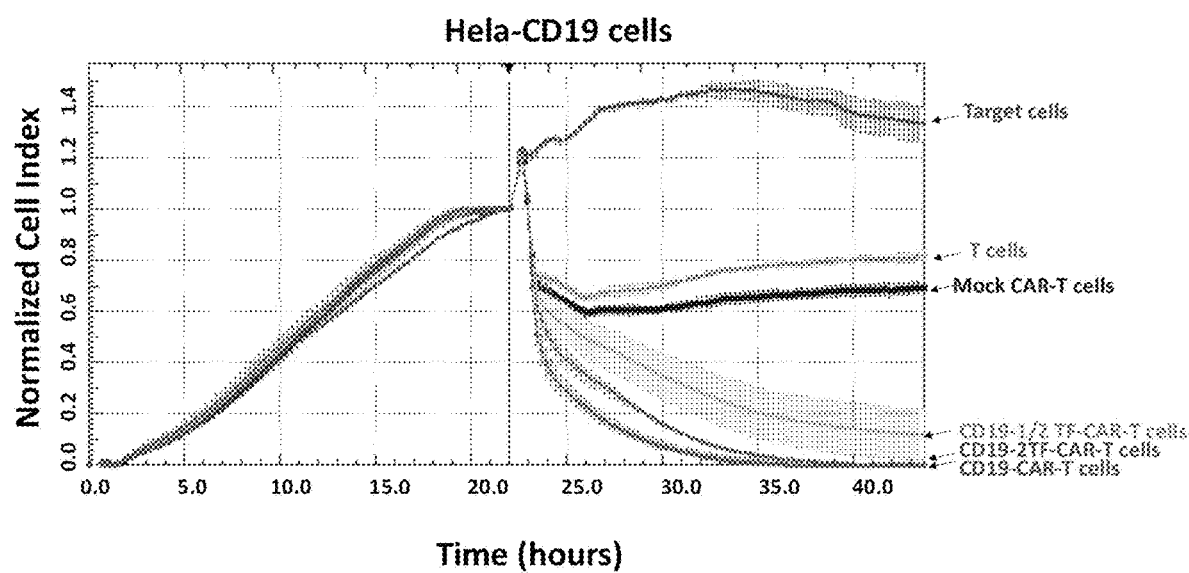
Figure 11:
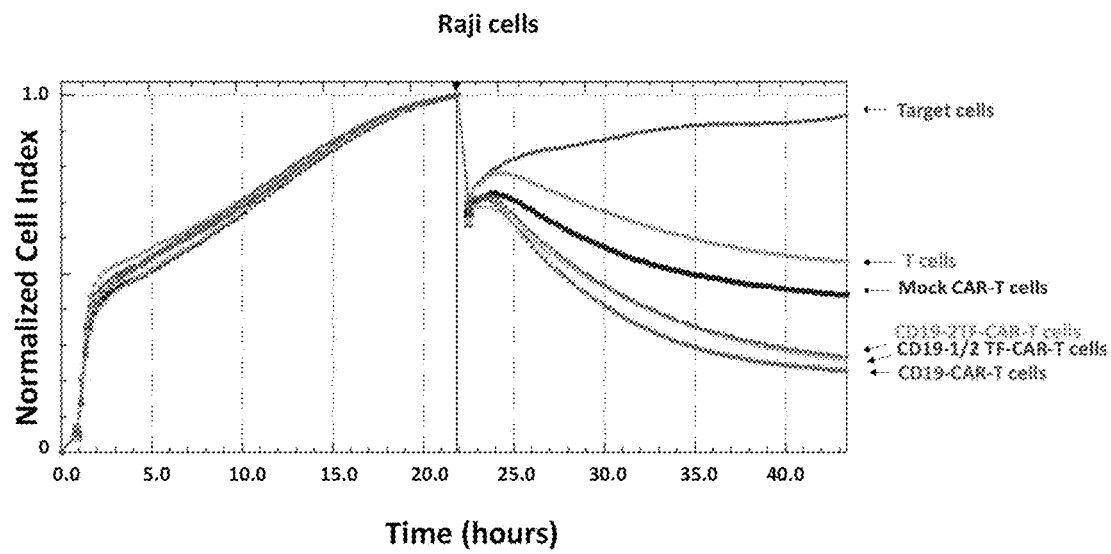
FIG. 11. CD19-1/2TF-CAR and CD19 2TF-CAR have same cytotoxic activity as CD19-CAR against target Raji cells. RTCA assay was used with target cells (E:T=10:1).

Example 19. CD19-1/2TF-CAR and CD19-2TF-CAR have Same Cytotoxic Activity as CD19-CAR Against Target Hela-CD19 Cells and Raji Cells To analyze if longer and shorter TF sequences generate CD19-TF-CAR with same cytotoxic activity as CD19-CAR, we used CD19-1/2TF and CD19-2xTF as shown in FIG. 2 to test against CD19-positive target cells. Both CD19-1/2TF- and CD19-2TF-CAR-T cells were equally cytotoxic with CD19-CAR-T cells against target Hela-CD19 cells (FIG. 10) and lymphoma Raji cells (FIG. 11). This suggest that 1/2 TF and 2 TF can be used to generate CAR-T cells with same cytotoxic activity as parental CD19-CAR-T cells.

Figure 12:
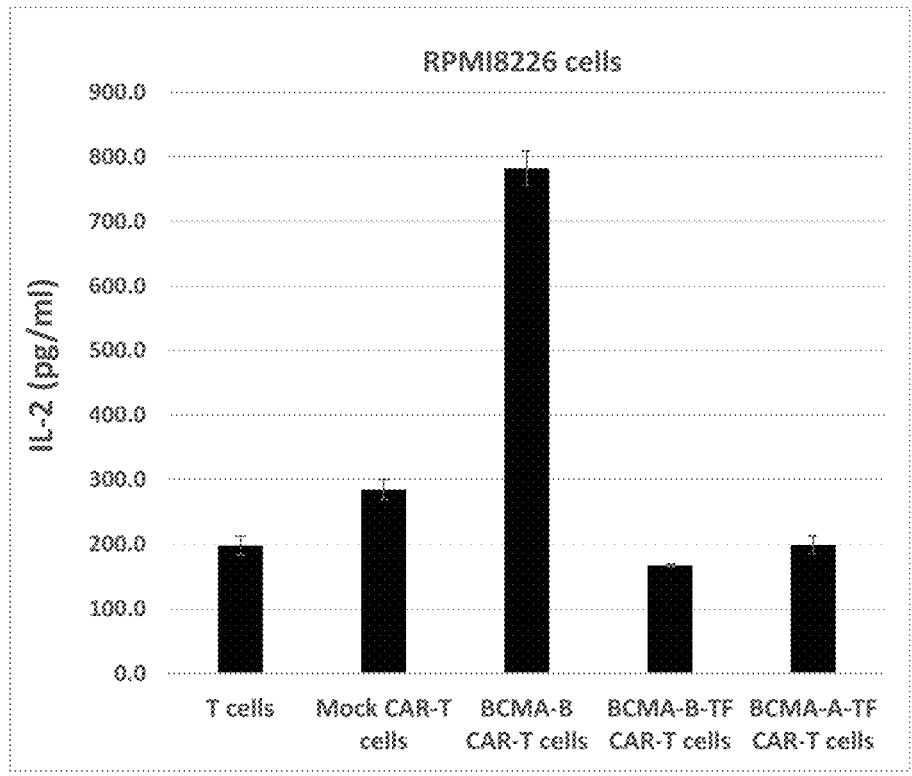
FIG. 12. Secretion of IL-2 is significantly less by BCMA-TF-CAR-T cells than by BCMA-CAR-T cells against multiple myeloma cells. BCMA-A-CAR-T cells had similar secretion of IL-2 as BCMA-B-CAR-T cells (now shown). p<0.05, BCMA (Clones A and B)-TF-CAR-T cells secreted significantly less IL-2 than BCMA-Clone B-CAR-T cells.

Example 20. BCMA-TF-CAR-T Cells Secrete Significantly Less IL-2 than BCMA-CAR-T Cells FIG. 12. shows that secretion of IL-2 by BCMA-TF-CAR-T cells is significantly less than by BCMA-CAR-T cells against multiple myeloma cells RPMI8226 cells.

Figure 13A:
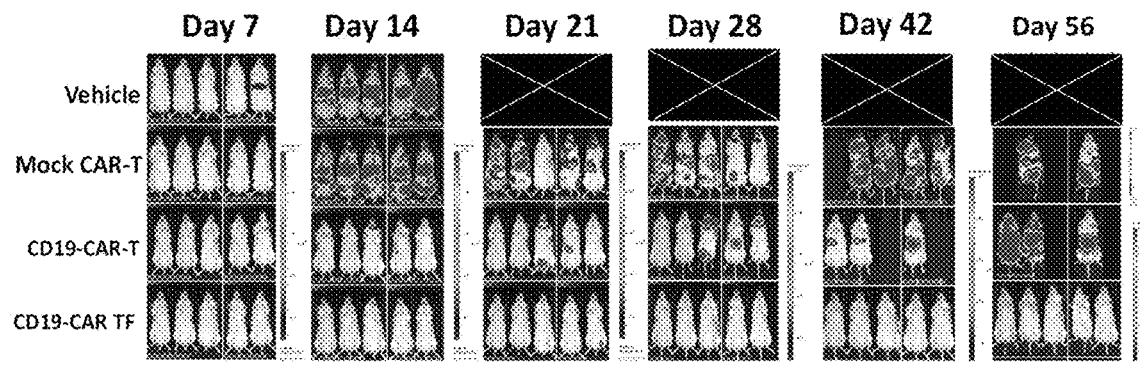
FIGS. 13A-D. CD19-TF-CAR-Tcells significantly decrease Raji tumor growth in vivo and prolong mouse survival. A. IVIS imaging shows significantly decreased number of Raji-luciferase-positive cells in case of CAR-T-treated mice. B. Shows quantification of the BLI (bioluminescence) signal. C. Kaplan-Meier survival plot. P<0.05 CAR-T treated versus PB S-treated mice. D, Detection of CD19-CAR-T cells in mouse blood in Raji xenograft mouse model after treatment with CAR-T cells. FACS staining with either CD19scFv Ab (for CD19) and TF antibodies for CD19-TF-CAR-T cells) was performed. Y-axis shows increased number of CD19-CAR-T cells in mouse blood.
Figure 13B:
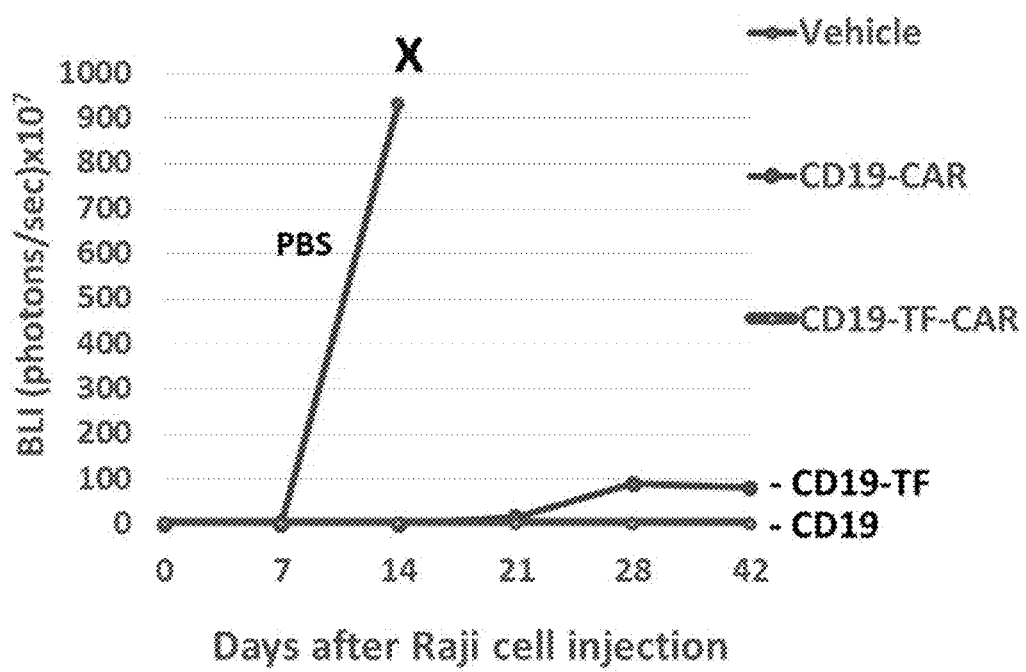
Figure 13C:
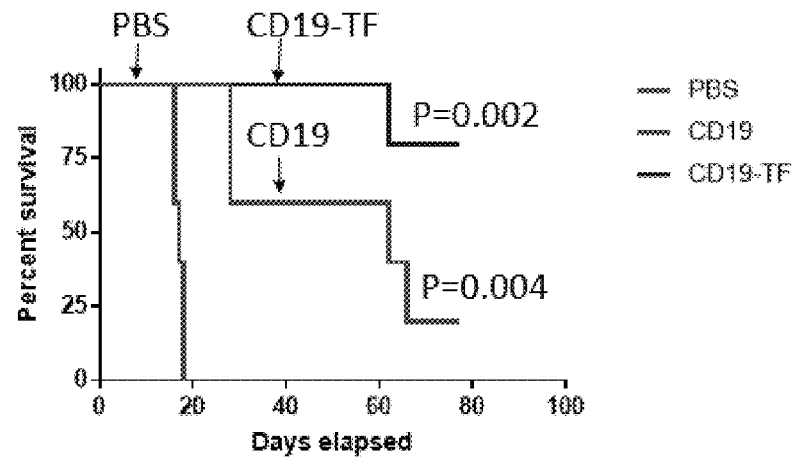
Figure 13D:
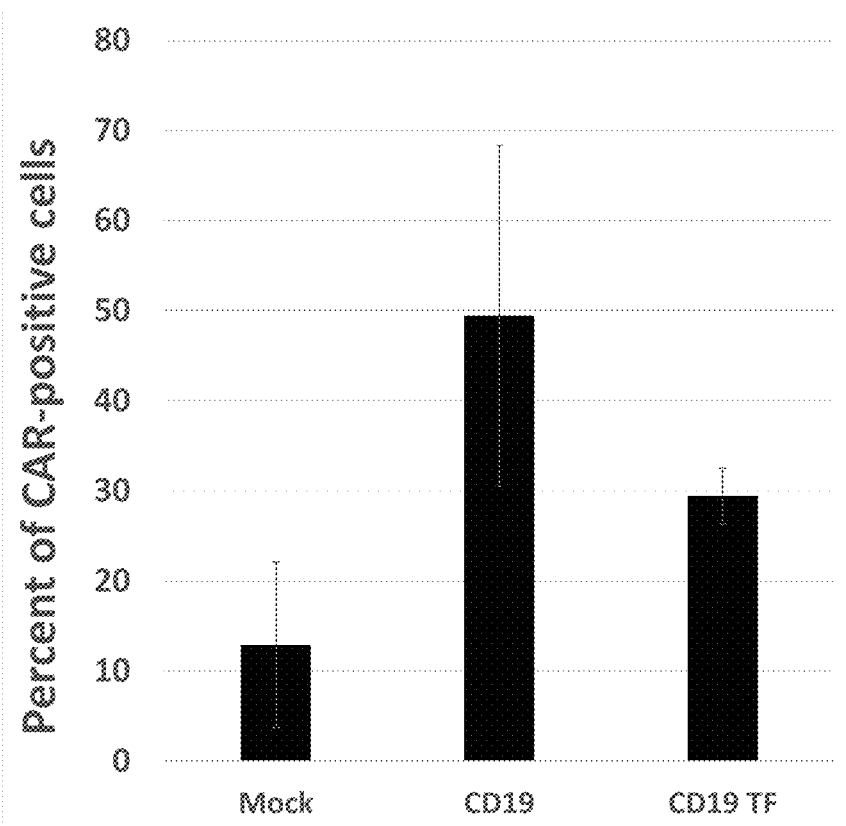

Example 21. CD19-TF-CAR-T Cells Significantly Decrease Raji Xenograft Tumor Growth Raji-luciferase positive cells were injected into NSG mice by i.v (intravenously) and then next day CD19-TF-CAR-T cells were injected by i.v. The CD19-(no TF)-CAR-T cells were also injected and PBS was used as controls. While PBS control mice died at day 21, CD19-CAR-T cell and CD19-TF-CAR-T cell-treated mice survived (FIGS. 13A-D). The imaging on FIG. 13 shows complete elimination of Raji-luciferase positive cells, and significant decrease of bioluminescence by CD19-TF-CAR-T cells. The survival of CD19-TF-CAR-T cell treated mice was better than CD19-CAR-T cell-treated mice (FIG. 13C). The CAR-T cells were detected in mice with either CD19scFv (for CD19-CAR-T cells) or TF antibodies (for CD19-TF-CAR-T cells) in mouse blood (FIG. 13D)

REFERENCES

1. Gross, G., and Eshhar, Z. (2016). Annu Rev Pharmacol Toxicol 56, 59-83.
2. Maus, M. V., Grupp, S. A., Porter, D. L., and June, C. H. (2014). Blood 123, 2625-2635.
3. Maus, M. V., Haas, A. R., Beatty, G. L., Albelda, S. M., Levine, B. L., Liu, X., Zhao, Y., Kalos, M., and June, C. H. (2013). Cancer Immunol Res 1, 26-31.
4. Kochenderfer, J. N., Dudley, M. E., Kassim, S. H., Somerville, R. P., Carpenter, R. O., Stetler-Stevenson, M., Yang, J. C., Phan, G. Q., Hughes, M. S., Sherry, R. M., et al. (2015). J Clin Oncol 33, 540-549.
5. Golubovskaya, V., and Wu, L. (2016). Cancers (Basel) 8.
6. Maus, M. V., and June, C. H. (2013). Clin Cancer Res 19, 1917-1919.
7. Maus, M. V., and June, C. H. (2014). Clin Cancer Res 20, 3899-3901.
8. Kochenderfer, J. N., and Rosenberg, S. A. (2013). Nat Rev Clin Oncol 10, 267-276.

What is claimed is:

1. A chimeric antigen receptor (CAR) comprising from N-terminal to C-terminal:
   an extracellular domain comprising
      a single-chain variable fragment (scFv) comprising VH and VL, wherein scFv binds to a tumor antigen,
      a human transferrin fragment having the amino acid sequence of KNPDPWAKNLNEKDY (SEQ ID NO: 1, TF), 2-5 TFs, or 1/2 TF having the amino sequence of KNLNEKDY (SEQ ID NO: 2), wherein the transferrin fragment is C-terminus to the scFv;
   a transmembrane domain; and
   an intracellular domain comprising:
      at least one co-stimulatory domains, and
      an activating domain.

2. The CAR according to claim 1, wherein the tumor antigen is selected from the group consisting of: CD19, CD22, BCMA, VEGFR-2, CD20, CD30, CD25, CD28, CD30, CD33, CD47, CD52, CD56, CD80, CD81, CD86, CD123, CD171, CD276, B7H4, CD133, EGFR, GPC3; PMSA, CD3, CEACAM6, c-Met, EGFRvIII, ErbB2/HER-2, ErbB3/HER3, ErbB4/HER-4, EphA2, IGF1R, GD2, O-acetyl GD2, O-acetyl GD3, GHRHR, GHR, FLT1, KDR, FLT4, CD44v6, CD151, CA125, CEA, CTLA-4, GITR, BTLA, TGFBR2, TGFBR1, IL6R, gp130, Lewis A, Lewis Y, TNFR1, TNFR2, PD1, PD-L1, PD-L2, HVEM, MAGE-A, mesothelin, NY-ESO-1, PSMA, RANK, ROR1, TNFRSF4, CD40, CD137, TWEAK-R, LTPR, LIFRP, LRP5, MUC1, TCRa, TCRp, TLR7, TLR9, PTCH1, WT-1, Robol, a, Frizzled, OX40, CD79b, and Notch-1-4.

3. The CAR according to claim 2, wherein the tumor antigen is CD19.

4. The CAR according to claim 3, wherein (a) the VH has the amino acid sequence of SEQ ID NO: 6 and VL has the amino acid sequence of SEQ ID NO: 4, or (b) the VH has the amino acid sequence of SEQ ID NO: 16 and the VL has the amino acid sequence of SEQ ID NO: 14.

5. The CAR according to claim 2, wherein the tumor antigen is CD22.

6. The CAR according to claim 5, wherein the VH has the amino acid sequence of SEQ ID NO: 17 and the VL has the amino acid sequence of SEQ ID NO: 18.

7. The CAR according to claim 2, wherein the tumor antigen is BCMA.

8. The CAR according to claim 7, wherein (a) the VH has the amino acid sequence of SEQ ID NO: 22 and the VL has the amino acid sequence of SEQ ID NO: 23, or (b) the VH has the amino acid sequence of SEQ ID NO: 26 and the VL has the amino acid sequence of SEQ ID NO: 27, or (c) the VH has the amino acid sequence of SEQ ID NO: 29 and the VL has the amino acid sequence of SEQ ID NO: 30, or (d) the VH has the amino acid sequence of SEQ ID NO: 31 and VL has the amino acid sequence of SEQ ID NO: 32.

9. The CAR according to claim 1, wherein the co-stimulatory domain is selected from the group consisting of CD28, 4-1BB, ICOS-1, CD27, OX-40, GITR and DAP10.

10. The CAR according to claim 1, wherein the co-stimulatory domain is CD28.

11. The CAR according to claim 1, wherein the human transferrin fragment has the amino acid sequence of SEQ ID NO: 1.

12. The CAR according to claim 11, which has the amino acid sequence of SEQ ID NO: 11 or at least 95% sequence identity thereof.

13. The CAR according to claim 1, wherein the human transferrin fragment has the amino acid sequence of 2 TF.

14. The CAR according to claim 13, which has the amino acid sequence of SEQ ID NO: 13 or at least 95% sequence identity thereof.

15. The CAR according to claim 1, wherein the human transferrin fragment has the amino acid sequence of SEQ ID NO: 2.

16. The CAR according to claim 15, which has the amino acid sequence of SEQ ID NO: 12 or at least 95% sequence identity thereof.

17. The CAR according to claim 1, wherein the scFv comprises from N-terminal to C-terminal the VL, a linker, and the VH, and the linker has the amino acid sequence of SEQ ID NO: 5.

* * * * *

```
                        SEQUENCE LISTING

<160> NUMBER OF SEQ ID NOS: 32

<210> SEQ ID NO 1
<211> LENGTH: 15
<212> TYPE: PRT
<213> ORGANISM: Homo sapiens

<400> SEQUENCE: 1

Lys Asn Pro Asp Pro Trp Ala Lys Asn Leu Asn Glu Lys Asp Tyr
1               5                   10                  15

<210> SEQ ID NO 2
<211> LENGTH: 8
<212> TYPE: PRT
<213> ORGANISM: Homo sapiens

<400> SEQUENCE: 2

Lys Asn Leu Asn Glu Lys Asp Tyr
1               5

<210> SEQ ID NO 3
<211> LENGTH: 22
<212> TYPE: PRT
<213> ORGANISM: Mus musculus

<400> SEQUENCE: 3

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 4
<211> LENGTH: 107
<212> TYPE: PRT
<213> ORGANISM: Homo sapiens

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
```

100                 105

<210> SEQ ID NO 5
<211> LENGTH: 18
<212> TYPE: PRT
<213> ORGANISM: Artificial Sequence
<220> FEATURE:
<223> OTHER INFORMATION: synthetic

<400> SEQUENCE: 5

Gly Ser Thr Ser Gly Ser Gly Lys Pro Gly Ser Gly Glu Gly Ser Thr
1               5                   10                  15

Lys Gly

<210> SEQ ID NO 6
<211> LENGTH: 122
<212> TYPE: PRT
<213> ORGANISM: Mus musculus

<400> SEQUENCE: 6

Glu Val Lys Leu Gln Glu Ser Gly Pro Gly Leu Val Ala Pro Ser Gln
1               5                   10                  15

Ser Leu Ser Val Thr Cys Thr Val Ser Gly Val Ser Leu Pro Asp Tyr
            20                  25                  30

Gly Val Ser Trp Ile Arg Gln Pro Pro Arg Lys Gly Leu Glu Trp Leu
        35                  40                  45

Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Glu Thr Asn Ser Leu Gln Thr Asp Asp Thr Ala Ile Tyr Tyr
                85                  90                  95

Cys Ala Lys His Tyr Tyr Tyr Gly Gly Ser Tyr Ala Met Asp Tyr Trp
            100                 105                 110

Gly Gln Gly Thr Ser Val Thr Val Ser Ser
        115                 120

<210> SEQ ID NO 7
<211> LENGTH: 39
<212> TYPE: PRT
<213> ORGANISM: Homo sapiens

<400> SEQUENCE: 7

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 8
<211> LENGTH: 27
<212> TYPE: PRT
<213> ORGANISM: Homo sapiens

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 41
<212> TYPE: PRT
<213> ORGANISM: Homo sapiens

<400> SEQUENCE: 9

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 10
<211> LENGTH: 84
<212> TYPE: PRT
<213> ORGANISM: Homo sapiens

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys

<210> SEQ ID NO 11
<211> LENGTH: 504
<212> TYPE: PRT
<213> ORGANISM: Mus musculus

<400> SEQUENCE: 11

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
            85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
        130                 135                 140

Thr Lys Gly Glu Val Lys Leu Gln Glu Ser Gly Pro Gly Leu Val Ala

```
            145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Lys Asn
                260                 265                 270

Pro Asp Pro Trp Ala Lys Asn Leu Asn Glu Lys Asp Tyr Ile Glu Val
            275                 280                 285

Met Tyr Pro Pro Pro Tyr Leu Asp Asn Glu Lys Ser Asn Gly Thr Ile
        290                 295                 300

Ile His Val Lys Gly Lys His Leu Cys Pro Ser Pro Leu Phe Pro Gly
305                 310                 315                 320

Pro Ser Lys Pro Phe Trp Val Leu Val Val Val Gly Gly Val Leu Ala
                325                 330                 335

Cys Tyr Ser Leu Leu Val Thr Val Ala Phe Ile Ile Phe Trp Val Arg
                340                 345                 350

Ser Lys Arg Ser Arg Leu Leu His Ser Asp Tyr Met Asn Met Thr Pro
                355                 360                 365

Arg Arg Pro Gly Pro Thr Arg Lys His Tyr Gln Pro Tyr Ala Pro Pro
            370                 375                 380

Arg Asp Phe Ala Ala Tyr Arg Ser Arg Val Lys Phe Ser Arg Ser Ala
385                 390                 395                 400

Asp Ala Pro Ala Tyr Gln Gln Gly Gln Asn Gln Leu Tyr Asn Glu Leu
                405                 410                 415

Asn Leu Gly Arg Arg Glu Glu Tyr Asp Val Leu Asp Lys Arg Arg Gly
            420                 425                 430

Arg Asp Pro Glu Met Gly Gly Lys Pro Arg Arg Lys Asn Pro Gln Glu
        435                 440                 445

Gly Leu Tyr Asn Glu Leu Gln Lys Asp Lys Met Ala Glu Ala Tyr Ser
    450                 455                 460

Glu Ile Gly Met Lys Gly Glu Arg Arg Arg Gly Lys Gly His Asp Gly
465                 470                 475                 480

Leu Tyr Gln Gly Leu Ser Thr Ala Thr Lys Asp Thr Tyr Asp Ala Leu
                485                 490                 495

His Met Gln Ala Leu Pro Pro Arg
            500

<210> SEQ ID NO 12
<211> LENGTH: 497
<212> TYPE: PRT
<213> ORGANISM: Mus musculus

<400> SEQUENCE: 12

Met Leu Leu Leu Val Thr Ser Leu Leu Leu Cys Glu Leu Pro His Pro
1               5                   10                  15
```

-continued

Ala Phe Leu Leu Ile Pro Asp Ile Gln Met Thr Gln Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ala Lys Asn
            260                 265                 270

Leu Asn Glu Lys Asp Tyr Ile Glu Val Met Tyr Pro Pro Pro Tyr Leu
        275                 280                 285

Asp Asn Glu Lys Ser Asn Gly Thr Ile Ile His Val Lys Gly Lys His
    290                 295                 300

Leu Cys Pro Ser Pro Leu Phe Pro Gly Pro Ser Lys Pro Phe Trp Val
305                 310                 315                 320

Leu Val Val Val Gly Gly Val Leu Ala Cys Tyr Ser Leu Leu Val Thr
                325                 330                 335

Val Ala Phe Ile Ile Phe Trp Val Arg Ser Lys Arg Ser Arg Leu Leu
            340                 345                 350

His Ser Asp Tyr Met Asn Met Thr Pro Arg Arg Pro Gly Pro Thr Arg
        355                 360                 365

Lys His Tyr Gln Pro Tyr Ala Pro Pro Arg Asp Phe Ala Ala Tyr Arg
    370                 375                 380

Ser Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln

```
                435                 440                 445
Lys Asp Lys Met Ala Glu Ala Tyr Ser Glu Ile Gly Met Lys Gly Glu
            450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg

<210> SEQ ID NO 13
<211> LENGTH: 519
<212> TYPE: PRT
<213> ORGANISM: Mus musculus

<400> SEQUENCE: 13

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Ala Ala Ala Lys Asn
            260                 265                 270

Pro Asp Pro Trp Ala Lys Asn Leu Asn Glu Lys Asp Tyr Lys Asn Pro
        275                 280                 285

Asp Pro Trp Ala Lys Asn Leu Asn Glu Lys Asp Tyr Ile Glu Val Met
    290                 295                 300

Tyr Pro Pro Pro Tyr Leu Asp Asn Glu Lys Ser Asn Gly Thr Ile Ile
```

```
            305                 310                 315                 320
His Val Lys Gly Lys His Leu Cys Pro Ser Pro Leu Phe Pro Gly Pro
                325                 330                 335

Ser Lys Pro Phe Trp Val Leu Val Val Gly Gly Val Leu Ala Cys
            340                 345                 350

Tyr Ser Leu Leu Val Thr Val Ala Phe Ile Ile Phe Trp Val Arg Ser
                355                 360                 365

Lys Arg Ser Arg Leu Leu His Ser Asp Tyr Met Asn Met Thr Pro Arg
            370                 375                 380

Arg Pro Gly Pro Thr Arg Lys His Tyr Gln Pro Tyr Ala Pro Pro Arg
385                 390                 395                 400

Asp Phe Ala Ala Tyr Arg Ser Arg Val Lys Phe Ser Arg Ser Ala Asp
                405                 410                 415

Ala Pro Ala Tyr Gln Gln Gly Gln Asn Gln Leu Tyr Asn Glu Leu Asn
            420                 425                 430

Leu Gly Arg Arg Glu Glu Tyr Asp Val Leu Asp Lys Arg Arg Gly Arg
            435                 440                 445

Asp Pro Glu Met Gly Gly Lys Pro Arg Arg Lys Asn Pro Gln Glu Gly
            450                 455                 460

Leu Tyr Asn Glu Leu Gln Lys Asp Lys Met Ala Glu Ala Tyr Ser Glu
465                 470                 475                 480

Ile Gly Met Lys Gly Glu Arg Arg Arg Gly Lys Gly His Asp Gly Leu
                485                 490                 495

Tyr Gln Gly Leu Ser Thr Ala Thr Lys Asp Thr Tyr Asp Ala Leu His
            500                 505                 510

Met Gln Ala Leu Pro Pro Arg
            515

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gly Gly Thr Lys Val Glu Ile Lys
            100                 105

<210> SEQ ID NO 15
<211> LENGTH: 18
<212> TYPE: PRT
<213> ORGANISM: Artificial Sequence
<220> FEATURE:
<223> OTHER INFORMATION: synthetic

<400> SEQUENCE: 15
```

-continued

```
Gly Ser Thr Ser Gly Ser Gly Lys Pro Gly Ser Gly Glu Gly Ser Thr
1               5                   10                  15

Lys Gly

<210> SEQ ID NO 16
<211> LENGTH: 120
<212> TYPE: PRT
<213> ORGANISM: Homo sapiens

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Leu Pro Asp Tyr
            20                  25                  30

Gly Val Ser Trp Ile Arg Gln Pro Pro Gly Lys Gly Leu Glu Trp Ile
        35                  40                  45

Gly Val Ile Trp Gly Ser Glu Thr Thr Tyr Tyr Asn Ser Ala Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Leu Val Thr Val Ser Ser
        115                 120

<210> SEQ ID NO 17
<211> LENGTH: 124
<212> TYPE: PRT
<213> ORGANISM: Homo sapiens

<400> SEQUENCE: 17

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Glu Val Thr Gly Asp Leu Glu Asp Ala Phe Asp
            100                 105                 110

Ile Trp Gly Gln Gly Thr Met Val Thr Val Ser Ser
        115                 120

<210> SEQ ID NO 18
<211> LENGTH: 107
<212> TYPE: PRT
<213> ORGANISM: Homo sapiens

<400> SEQUENCE: 18

Asp Ile Gln Met Thr Gln Ser Pro Ser Ser Leu Ser Ala Ser Val Gly
```

```
                1               5                   10                  15
Asp Arg Val Thr Ile Thr Cys Arg Ala Ser Gln Thr Ile Trp Ser Tyr
                        20                  25                  30

Leu Asn Trp Tyr Gln Gln Arg Pro Gly Lys Ala Pro Asn Leu Leu Ile
            35                  40                  45

Tyr Ala Ala Ser Ser Leu Gln Ser Gly Val Pro Ser Arg Phe Ser Gly
        50                  55                  60

Arg Gly Ser Gly Thr Asp Phe Thr Leu Thr Ile Ser Ser Leu Gln Ala
65                      70                  75                  80

Glu Asp Phe Ala Thr Tyr Tyr Cys Gln Gln Ser Tyr Ser Ile Pro Gln
                        85                  90                  95

Thr Phe Gly Gln Gly Thr Lys Leu Glu Ile Lys
                    100                 105

<210> SEQ ID NO 19
<211> LENGTH: 15
<212> TYPE: PRT
<213> ORGANISM: Artificial Sequence
<220> FEATURE:
<223> OTHER INFORMATION: synthetic

<400> SEQUENCE: 19

Gly Gly Gly Gly Ser Gly Gly Gly Ser Gly Gly Gly Ser
1               5                   10                  15

<210> SEQ ID NO 20
<211> LENGTH: 502
<212> TYPE: PRT
<213> ORGANISM: Homo sapiens

<400> SEQUENCE: 20

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
                        20                  25                  30

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                      70                  75                  80

Trp Tyr Asn Asp Tyr Ala Val Ser Val Lys Ser Arg Ile Thr Ile Asn
                        85                  90                  95

Pro Asp Thr Ser Lys Asn Gln Phe Ser Leu Gln Leu Asn Ser Val Thr
                    100                 105                 110

Pro Glu Asp Thr Ala Val Tyr Tyr Cys Ala Arg Glu Val Thr Gly Asp
                115                 120                 125

Leu Glu Asp Ala Phe Asp Ile Trp Gly Gln Gly Thr Met Val Thr Val
            130                 135                 140

Ser Ser Gly Gly Gly Gly Ser Gly Gly Gly Gly Ser Gly Gly Gly Gly
145                 150                 155                 160

Ser Asp Ile Gln Met Thr Gln Ser Pro Ser Ser Leu Ser Ala Ser Val
                        165                 170                 175

Gly Asp Arg Val Thr Ile Thr Cys Arg Ala Ser Gln Thr Ile Trp Ser
                    180                 185                 190

Tyr Leu Asn Trp Tyr Gln Gln Arg Pro Gly Lys Ala Pro Asn Leu Leu
                195                 200                 205
```

Ile Tyr Ala Ala Ser Ser Leu Gln Ser Gly Val Pro Ser Arg Phe Ser
210                 215                 220

Gly Arg Gly Ser Gly Thr Asp Phe Thr Leu Thr Ile Ser Ser Leu Gln
225                 230                 235                 240

Ala Glu Asp Phe Ala Thr Tyr Tyr Cys Gln Gln Ser Tyr Ser Ile Pro
            245                 250                 255

Gln Thr Phe Gly Gln Gly Thr Lys Leu Glu Ile Lys Lys Asn Pro Asp
            260                 265                 270

Pro Trp Ala Lys Asn Leu Asn Glu Lys Asp Tyr Ile Glu Val Met Tyr
        275                 280                 285

Pro Pro Pro Tyr Leu Asp Asn Glu Lys Ser Asn Gly Thr Ile Ile His
    290                 295                 300

Val Lys Gly Lys His Leu Cys Pro Ser Pro Leu Phe Pro Gly Pro Ser
305                 310                 315                 320

Lys Pro Phe Trp Val Leu Val Val Val Gly Gly Val Leu Ala Cys Tyr
                325                 330                 335

Ser Leu Leu Val Thr Val Ala Phe Ile Ile Phe Trp Val Arg Ser Lys
            340                 345                 350

Arg Ser Arg Leu Leu His Ser Asp Tyr Met Asn Met Thr Pro Arg Arg
            355                 360                 365

Pro Gly Pro Thr Arg Lys His Tyr Gln Pro Tyr Ala Pro Pro Arg Asp
        370                 375                 380

Phe Ala Ala Tyr Arg Ser Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
            405                 410                 415

Gly Arg Arg Glu Glu Tyr Asp Val Leu Asp Lys Arg Arg Gly Arg Asp
        420                 425                 430

Pro Glu Met Gly Gly Lys Pro Arg Arg Lys Asn Pro Gln Glu Gly Leu
    435                 440                 445

Tyr Asn Glu Leu Gln Lys Asp Lys Met Ala Glu Ala Tyr Ser Glu Ile
    450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
            485                 490                 495

Gln Ala Leu Pro Pro Arg
            500

<210> SEQ ID NO 21
<211> LENGTH: 21
<212> TYPE: PRT
<213> ORGANISM: Homo sapiens

<400> SEQUENCE: 21

Met Ala Leu Pro Val Thr Ala Leu Leu Leu Pro Leu Ala Leu Leu Leu
1               5                   10                  15

His Ala Ala Arg Pro
            20

<210> SEQ ID NO 22
<211> LENGTH: 112
<212> TYPE: PRT
<213> ORGANISM: Mus musculus

<400> SEQUENCE: 22

```
Gln Val Gln Val Val Glu Ser Gly Gly Gly Leu Val Lys Pro Gly
1               5                   10                  15

Ser Leu Lys Leu Ser Cys Val Val Ser Gly Phe Ala Phe Ser Ser Tyr
            20                  25                  30

Asp Met Ser Trp Val Arg Gln Thr Pro Glu Lys Arg Leu Glu Trp Val
            35                  40                  45

Ala Tyr Ile Asn Ser Gly Gly Tyr Ile Thr Tyr Tyr Leu Asp Thr Val
        50                  55                  60

Lys Gly Arg Phe Thr Ile Ser Arg Asp Asn Ala Lys Asn Ile Leu Tyr
65                  70                  75                  80

Leu Gln Met Asn Ser Leu Lys Ser Glu Asp Ser Ala Leu Tyr Tyr Cys
                85                  90                  95

Val Pro Gly Phe Ala His Trp Gly Gln Gly Thr Leu Val Ile Val Ser
            100                 105                 110
```

<210> SEQ ID NO 23
<211> LENGTH: 112
<212> TYPE: PRT
<213> ORGANISM: Mus musculus

<400> SEQUENCE: 23

```
Asp Ile Val Met Thr Gln Ala Ala Pro Ser Val Pro Val Thr Pro Gly
1               5                   10                  15

Glu Ser Val Ser Ile Ser Cys Arg Ser Asn Lys Ser Leu Leu His Ser
            20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
        50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110
```

<210> SEQ ID NO 24
<211> LENGTH: 49
<212> TYPE: PRT
<213> ORGANISM: Homo sapiens

<400> SEQUENCE: 24

```
Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Lys
            35                  40                  45

Pro
```

<210> SEQ ID NO 25
<211> LENGTH: 509
<212> TYPE: PRT
<213> ORGANISM: Mus musculus

<400> SEQUENCE: 25

Met Ala Leu Pro Val Thr Ala Leu Leu Leu Pro Leu Ala Leu Leu Leu

-continued

```
1               5                   10                  15
His Ala Ala Arg Pro Ala Ser Gln Val Gln Val Val Glu Ser Gly Gly
                20                  25                  30
Gly Leu Val Lys Pro Gly Gly Ser Leu Lys Leu Ser Cys Val Val Ser
                35                  40                  45
Gly Phe Ala Phe Ser Ser Tyr Asp Met Ser Trp Val Arg Gln Thr Pro
 50                  55                  60
Glu Lys Arg Leu Glu Trp Val Ala Tyr Ile Asn Ser Gly Gly Tyr Ile
 65                  70                  75                  80
Thr Tyr Tyr Leu Asp Thr Val Lys Gly Arg Phe Thr Ile Ser Arg Asp
                85                  90                  95
Asn Ala Lys Asn Ile Leu Tyr Leu Gln Met Asn Ser Leu Lys Ser Glu
                100                 105                 110
Asp Ser Ala Leu Tyr Tyr Cys Val Pro Gly Phe Ala His Trp Gly Gln
                115                 120                 125
Gly Thr Leu Val Ile Val Ser Gly Gly Gly Ser Gly Gly Gly Gly
                130                 135                 140
Ser Gly Gly Gly Gly Ser Asp Ile Val Met Thr Gln Ala Ala Pro Ser
145                 150                 155                 160
Val Pro Val Thr Pro Gly Glu Ser Val Ser Ile Ser Cys Arg Ser Asn
                165                 170                 175
Lys Ser Leu Leu His Ser Asn Gly Asn Thr Tyr Leu Tyr Trp Phe Leu
                180                 185                 190
Gln Arg Pro Gly Gln Ser Pro Gln Leu Leu Ile Tyr Arg Met Ser Asn
                195                 200                 205
Leu Ala Ser Gly Val Pro Asp Arg Phe Ser Gly Ser Gly Ser Gly Thr
210                 215                 220
Ala Phe Thr Leu Arg Ile Ser Arg Val Glu Ala Glu Asp Val Gly Val
225                 230                 235                 240
Tyr Tyr Cys Met Gln His Leu Glu Tyr Pro Tyr Thr Phe Gly Gly Gly
                245                 250                 255
Thr Lys Leu Glu Ile Lys Lys Asn Pro Asp Pro Trp Ala Lys Asn Leu
                260                 265                 270
Asn Glu Lys Asp Tyr Leu Glu Lys Pro Thr Thr Thr Pro Ala Pro Arg
                275                 280                 285
Pro Pro Thr Pro Ala Pro Thr Ile Ala Ser Gln Pro Leu Ser Leu Arg
                290                 295                 300
Pro Glu Ala Ser Arg Pro Ala Ala Gly Gly Ala Val His Thr Arg Gly
305                 310                 315                 320
Leu Asp Phe Ala Ser Asp Lys Pro Phe Trp Val Leu Val Val Val Gly
                325                 330                 335
Gly Val Leu Ala Cys Tyr Ser Leu Leu Val Thr Val Ala Phe Ile Ile
                340                 345                 350
Phe Trp Val Arg Ser Lys Arg Ser Arg Leu Leu His Ser Asp Tyr Met
                355                 360                 365
Asn Met Thr Pro Arg Arg Pro Gly Pro Thr Arg Lys His Tyr Gln Pro
                370                 375                 380
Tyr Ala Pro Pro Arg Asp Phe Ala Ala Tyr Arg Ser Arg Val Lys Phe
385                 390                 395                 400
Ser Arg Ser Ala Asp Ala Pro Ala Tyr Gln Gln Gly Gln Asn Gln Leu
                405                 410                 415
Tyr Asn Glu Leu Asn Leu Gly Arg Arg Glu Glu Tyr Asp Val Leu Asp
                420                 425                 430
```

```
Lys Arg Arg Gly Arg Asp Pro Glu Met Gly Lys Pro Gln Arg Arg
            435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 26
<211> LENGTH: 112
<212> TYPE: PRT
<213> ORGANISM: Mus musculus

<400> SEQUENCE: 26

Gln Val Gln Val Val Glu Ser Gly Gly Gly Leu Met Lys Pro Gly Gly
1               5                   10                  15

Ser Leu Lys Leu Ser Cys Val Val Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Tyr Ile Asn Ser Gly Gly Tyr Ile Thr Tyr Tyr Leu Asp Thr Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Lys Ser Glu Asp Ser Ala Leu Tyr Tyr Cys
                85                  90                  95

Val Pro Gly Phe Ala His Trp Gly Gln Gly Thr Leu Val Ile Val Ser
            100                 105                 110

<210> SEQ ID NO 27
<211> LENGTH: 112
<212> TYPE: PRT
<213> ORGANISM: Mus musculus

<400> SEQUENCE: 27

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Arg
            20                  25                  30

Asn Gly Asn Ser Tyr Leu His Trp Tyr Leu Gln Arg Pro Gly Gln Ser
        35                  40                  45

Pro Lys Leu Leu Ile Tyr Lys Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Arg Arg Val Glu Ala Glu Asp Leu Gly Val Tyr Phe Cys Ser Gln Ser
                85                  90                  95

Thr His Phe Pro Tyr Thr Phe Gly Gly Gly Thr Met Leu Glu Ile Lys
            100                 105                 110

<210> SEQ ID NO 28
<211> LENGTH: 509
<212> TYPE: PRT
<213> ORGANISM: Mus musculus
```

<400> SEQUENCE: 28

```
Met Ala Leu Pro Val Thr Ala Leu Leu Pro Leu Ala Leu Leu Leu
1               5                   10                  15

His Ala Ala Arg Pro Ala Ser Gln Val Gln Val Glu Ser Gly Gly
                20                  25                  30

Gly Leu Met Lys Pro Gly Gly Ser Leu Lys Leu Ser Cys Val Val Ser
            35                  40                  45

Gly Phe Ala Phe Ser Ser Tyr Asp Met Ser Trp Val Arg Gln Thr Pro
    50                  55                  60

Glu Lys Arg Leu Glu Trp Val Ala Tyr Ile Asn Ser Gly Gly Tyr Ile
65              70                  75                  80

Thr Tyr Tyr Leu Asp Thr Val Lys Gly Arg Phe Thr Ile Ser Arg Asp
                85                  90                  95

Asn Ala Lys Lys Ser Leu Tyr Leu Gln Met Asn Ser Leu Lys Ser Glu
                100                 105                 110

Asp Ser Ala Leu Tyr Tyr Cys Val Pro Gly Phe Ala His Trp Gly Gln
            115                 120                 125

Gly Thr Leu Val Ile Val Ser Gly Gly Gly Ser Gly Gly Gly Gly
    130                 135                 140

Ser Gly Gly Gly Gly Ser Asp Val Val Met Thr Gln Thr Pro Leu Ser
145                 150                 155                 160

Leu Pro Val Ser Leu Gly Asp Gln Ala Ser Ile Ser Cys Arg Ser Ser
                165                 170                 175

Gln Ser Leu Val His Arg Asn Gly Asn Ser Tyr Leu His Trp Tyr Leu
            180                 185                 190

Gln Arg Pro Gly Gln Ser Pro Lys Leu Leu Ile Tyr Lys Val Ser Ser
        195                 200                 205

Arg Phe Ser Gly Val Pro Asp Arg Phe Ser Gly Ser Gly Ser Gly Thr
210                 215                 220

Asp Phe Thr Leu Lys Ile Arg Arg Val Glu Ala Glu Asp Leu Gly Val
225                 230                 235                 240

Tyr Phe Cys Ser Gln Ser Thr His Phe Pro Tyr Thr Phe Gly Gly Gly
            245                 250                 255

Thr Met Leu Glu Ile Lys Lys Asn Pro Asp Pro Trp Ala Lys Asn Leu
        260                 265                 270

Asn Glu Lys Asp Tyr Leu Glu Lys Pro Thr Thr Thr Pro Ala Pro Arg
            275                 280                 285

Pro Pro Thr Pro Ala Pro Thr Ile Ala Ser Gln Pro Leu Ser Leu Arg
        290                 295                 300

Pro Glu Ala Ser Arg Pro Ala Ala Gly Gly Ala Val His Thr Arg Gly
305                 310                 315                 320

Leu Asp Phe Ala Ser Asp Lys Pro Phe Trp Val Leu Val Val Val Gly
            325                 330                 335

Gly Val Leu Ala Cys Tyr Ser Leu Leu Val Thr Val Ala Phe Ile Ile
        340                 345                 350

Phe Trp Val Arg Ser Lys Arg Ser Arg Leu Leu His Ser Asp Tyr Met
            355                 360                 365

Asn Met Thr Pro Arg Arg Pro Gly Pro Thr Arg Lys His Tyr Gln Pro
        370                 375                 380

Tyr Ala Pro Pro Arg Asp Phe Ala Ala Tyr Arg Ser Arg Val Lys Phe
385                 390                 395                 400

Ser Arg Ser Ala Asp Ala Pro Ala Tyr Gln Gln Gly Gln Asn Gln Leu
```

```
                        405                 410                 415

Tyr Asn Glu Leu Asn Leu Gly Arg Arg Glu Glu Tyr Asp Val Leu Asp
            420                 425                 430

Lys Arg Arg Gly Arg Asp Pro Glu Met Gly Gly Lys Pro Gln Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
465                 470                 475                 480

Lys Gly His Asp Gly Leu Tyr Gln Gly Leu Ser Thr Ala Thr Lys Asp
                485                 490                 495

Thr Tyr Asp Ala Leu His Met Gln Ala Leu Pro Pro Arg
            500                 505

<210> SEQ ID NO 29
<211> LENGTH: 116
<212> TYPE: PRT
<213> ORGANISM: Homo sapiens

<400> SEQUENCE: 29

Gln Leu Gln Gln Ser Gly Pro Glu Leu Val Lys Ser Gly Ala Ser Val
1               5                   10                  15

Lys Met Ser Cys Lys Ala Ser Gly Tyr Thr Phe Thr Ser Tyr Val Met
            20                  25                  30

His Trp Val Lys Gln Lys Pro Gly Gln Gly Leu Glu Trp Ile Gly Phe
        35                  40                  45

Ile Ile Pro Tyr Asn Asp Asp Thr Lys Tyr Asn Glu Lys Phe Lys Gly
    50                  55                  60

Lys Ala Ser Leu Thr Ser Asp Lys Ser Ser Thr Ala Phe Met Glu
65                  70                  75                  80

Leu Ser Ser Leu Thr Ser Glu Asp Ser Ala Val Tyr Tyr Cys Ala Arg
                85                  90                  95

Trp Asn Tyr Asp Gly Tyr Phe Asp Val Trp Gly Ala Gly Thr Thr Val
            100                 105                 110

Thr Val Ser Ser
        115

<210> SEQ ID NO 30
<211> LENGTH: 113
<212> TYPE: PRT
<213> ORGANISM: Homo sapiens

<400> SEQUENCE: 30

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ile
                85                  90                  95

Thr His Val Pro Tyr Thr Phe Gly Gly Gly Thr Lys Leu Glu Ile Arg
```

```
                   100                 105                 110

Arg

<210> SEQ ID NO 31
<211> LENGTH: 116
<212> TYPE: PRT
<213> ORGANISM: Homo sapiens

<400> SEQUENCE: 31

Gln Leu Gln Gln Ser Gly Pro Glu Leu Val Lys Ser Gly Ala Ser Val
1               5                   10                  15

Lys Met Ser Cys Lys Ala Ser Gly Tyr Thr Phe Thr Ser Tyr Val Met
            20                  25                  30

His Trp Val Lys Gln Lys Pro Gly Gln Gly Leu Glu Trp Ile Gly Phe
        35                  40                  45

Ile Ile Pro Tyr Asn Asp Asp Thr Lys Tyr Asn Glu Lys Phe Lys Gly
    50                  55                  60

Lys Ala Ser Leu Thr Ser Asp Lys Ser Ser Ser Thr Ala Tyr Met Glu
65                  70                  75                  80

Leu Ser Ser Leu Thr Ser Glu Asp Ser Ala Val Tyr Tyr Cys Ala Arg
                85                  90                  95

Trp Asp Phe Asp Gly Tyr Phe Asp Val Trp Gly Ala Gly Thr Thr Val
            100                 105                 110

Thr Val Ser Ser
            115

<210> SEQ ID NO 32
<211> LENGTH: 113
<212> TYPE: PRT
<213> ORGANISM: Homo sapiens

<400> SEQUENCE: 32

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ile
                85                  90                  95

Thr His Val Pro Tyr Thr Phe Gly Gly Gly Thr Lys Leu Glu Ile Arg
            100                 105                 110

Arg
```